US011492318B2

(12) United States Patent
Greuel

(10) Patent No.: US 11,492,318 B2
(45) Date of Patent: Nov. 8, 2022

(54) METHODS FOR MAKING FUNCTIONALIZED FLUORINATED MONOMERS, FLUORINATED MONOMERS, AND COMPOSITIONS FOR MAKING THE SAME

(71) Applicant: Etna-TEC, Ltd., Chagrin Falls, OH (US)

(72) Inventor: Michael P. Greuel, Solon, OH (US)

(73) Assignee: ETNA-TEC, LTD., Chagrin Falls, OH (US)

( * ) Notice: Subject to any disclaimer, the term of this patent is extended or adjusted under 35 U.S.C. 154(b) by 0 days.

(21) Appl. No.: 15/985,616

(22) Filed: May 21, 2018

(65) Prior Publication Data

US 2018/0334417 A1 Nov. 22, 2018

Related U.S. Application Data

(60) Provisional application No. 62/560,641, filed on Sep. 19, 2017, provisional application No. 62/508,835, filed on May 19, 2017.

(51) Int. Cl.

| | |
|---|---|
| C08F 22/38 | (2006.01) |
| C07C 231/12 | (2006.01) |
| C07C 311/04 | (2006.01) |
| C07C 319/20 | (2006.01) |
| C07C 323/01 | (2006.01) |
| C07C 323/12 | (2006.01) |
| C08F 8/18 | (2006.01) |
| C08F 14/18 | (2006.01) |
| C08F 222/08 | (2006.01) |
| C08F 22/02 | (2006.01) |
| C08F 22/18 | (2006.01) |
| C07C 43/13 | (2006.01) |
| C07C 303/28 | (2006.01) |
| C07C 227/10 | (2006.01) |

(Continued)

(52) U.S. Cl.
CPC .............. *C07C 41/03* (2013.01); *C07C 41/16* (2013.01); *C07C 41/24* (2013.01); *C07C 43/12* (2013.01); *C07C 43/137* (2013.01); *C07C 67/03* (2013.01); *C07C 67/08* (2013.01); *C07C 67/26* (2013.01); *C07C 69/63* (2013.01); *C07C 213/02* (2013.01); *C07C 227/10* (2013.01); *C07C 231/12* (2013.01); *C07C 235/08* (2013.01); *C07C 303/28* (2013.01); *C07C 303/40* (2013.01); *C07C 311/04* (2013.01); *C07C 319/20* (2013.01); *C07C 323/01* (2013.01); *C07C 323/12* (2013.01); *C08F 8/18* (2013.01); *C08F 14/18* (2013.01); *C08F 22/02* (2013.01); *C08F 22/18* (2013.01); *C08F 22/38* (2013.01); *C08F 222/08* (2013.01); *C08G 59/1438* (2013.01); *C08G 63/42* (2013.01); *C08G 63/6826* (2013.01); *C08G 63/91* (2013.01); *C08G 64/0233* (2013.01); *C08G 64/223* (2013.01); *C08G 64/42* (2013.01); *C08G 65/2639* (2013.01); *C08G 85/004* (2013.01); *C08L 27/12* (2013.01); *C07C 2601/14* (2017.05)

(58) Field of Classification Search
CPC ......... C07C 41/16; C07C 67/03; C07C 67/08; C07C 213/02
See application file for complete search history.

(56) References Cited

U.S. PATENT DOCUMENTS

| | | | |
|---|---|---|---|
| 2,723,999 | A | 11/1955 | Cowen et al. |
| 3,419,628 | A | 12/1968 | Kaufman et al. |

(Continued)

FOREIGN PATENT DOCUMENTS

| | | |
|---|---|---|
| CN | 1468649 A | 1/2004 |
| EP | 0 161 459 A1 | 11/1985 |

(Continued)

OTHER PUBLICATIONS

De Groot et al., "Synthesis of 18F-Fluoroalkyl-b-Glucosides and Their Evaluation as Tracers for Sodium-Dependent Glucose Transporters", Journal of Nuclear Medicine (2003), 44(12), 1973-1981 (Year: 2003).*

(Continued)

*Primary Examiner* — Nicole M. Buie-Hatcher
(74) *Attorney, Agent, or Firm* — Calderone Bullock LLC

(57) ABSTRACT

A method of making a functionalized fluorinated monomer for use in making oligomers and polymers that can be used to improve surface properties of polymer-derived systems, such as coatings. The method of making a functionalized fluorinated monomer includes reacting at least one fluorinated nucleophilic reactant, such as a fluorinated alcohol, with at least one compound containing at least one epoxide group. Other methods include reaction of a fluorinated alcohol with a cyclic carboxylic anhydride. In another embodiment, a method includes reacting a fluorinated mesylate, tosylate or triflate with an amine, alkoxide or phenoxide. In other embodiments, the method includes reacting a fluorinated alcohol with an alkyl halide, or reacting a fluorinated alkyl halide with an amine. The functionalized fluorinated monomers may be used as intermediates and reacted to modify the functional groups thereon. Further, the functionalized fluorinated monomers may be reacted to form polymers or oligomers, or with polymers or oligomers having functional groups to modify the polymer or oligomer through the functional group thereon.

24 Claims, No Drawings

(51) Int. Cl.

| | | |
|---|---|---|
| *C07C 67/03* | (2006.01) | |
| *C07C 41/03* | (2006.01) | |
| *C07C 67/26* | (2006.01) | |
| *C07C 69/63* | (2006.01) | |
| *C07C 235/08* | (2006.01) | |
| *C07C 303/40* | (2006.01) | |
| *C07C 41/16* | (2006.01) | |
| *C07C 67/08* | (2006.01) | |
| *C07C 213/02* | (2006.01) | |
| *C08G 59/14* | (2006.01) | |
| *C08G 64/02* | (2006.01) | |
| *C08G 63/91* | (2006.01) | |
| *C08G 64/42* | (2006.01) | |
| *C07C 41/24* | (2006.01) | |
| *C07C 43/12* | (2006.01) | |
| *C08G 63/42* | (2006.01) | |
| *C08G 63/682* | (2006.01) | |
| *C08G 64/22* | (2006.01) | |
| *C08G 65/26* | (2006.01) | |
| *C08G 85/00* | (2006.01) | |
| *C08L 27/12* | (2006.01) | |

(56) References Cited

U.S. PATENT DOCUMENTS

| | | | |
|---|---|---|---|
| 3,470,258 A | 9/1969 | Tesoro | |
| 3,654,245 A | 4/1972 | Kometani et al. | |
| 3,723,539 A | 3/1973 | Hamermesh et al. | |
| 3,761,524 A * | 9/1973 | Terrell | C07C 43/123 |
| | | | 568/683 |
| 3,883,665 A * | 5/1975 | Croix | C07C 43/12 |
| | | | 514/722 |
| 4,112,231 A | 5/1978 | Weibull et al. | |
| 4,182,846 A | 1/1980 | Saegusa et al. | |
| 4,490,561 A * | 12/1984 | Yang | C07C 41/03 |
| | | | 564/209 |
| 4,595,632 A | 6/1986 | Mayhan et al. | |
| 4,766,234 A * | 8/1988 | Wehowsky | C07C 275/62 |
| | | | 560/26 |
| 4,898,891 A | 2/1990 | Falk et al. | |
| 4,900,874 A | 2/1990 | Ihara et al. | |
| 5,004,790 A | 4/1991 | Harnish et al. | |
| 5,011,979 A * | 4/1991 | Gregorio | C07C 67/08 |
| | | | 560/223 |
| 5,342,903 A | 8/1994 | Wolleb et al. | |
| 5,362,848 A | 11/1994 | Archibald et al. | |
| 5,463,019 A | 10/1995 | Manser et al. | |
| 5,468,841 A | 11/1995 | Malik et al. | |
| 5,489,700 A | 2/1996 | Manser et al. | |
| 5,567,857 A | 10/1996 | Huang et al. | |
| 5,637,772 A | 6/1997 | Malik et al. | |
| 5,650,483 A | 7/1997 | Malik et al. | |
| 5,654,450 A | 8/1997 | Malik et al. | |
| 5,663,289 A | 9/1997 | Archibald et al. | |
| 5,668,250 A | 9/1997 | Malik et al. | |
| 5,668,251 A | 9/1997 | Malik et al. | |
| 5,679,282 A * | 10/1997 | Pauluth | C07C 25/18 |
| | | | 252/299.01 |
| 5,703,194 A | 12/1997 | Malik et al. | |
| 5,807,977 A | 9/1998 | Malik et al. | |
| 5,986,150 A | 11/1999 | Araki et al. | |
| 6,037,483 A | 3/2000 | Malik et al. | |
| 6,184,339 B1 | 2/2001 | Stansbury et al. | |
| 6,288,271 B1 | 9/2001 | Gutman et al. | |
| 6,380,351 B1 | 4/2002 | Malik et al. | |
| 6,403,760 B1 | 6/2002 | Weinert et al. | |
| 6,417,314 B1 | 7/2002 | Malik et al. | |
| 6,448,368 B1 | 9/2002 | Malik et al. | |
| 6,465,565 B1 | 10/2002 | Garcia et al. | |
| 6,465,566 B2 | 10/2002 | Garcia et al. | |
| 6,479,623 B1 | 11/2002 | Malik et al. | |
| 6,579,966 B1 | 6/2003 | Weinert et al. | |
| 6,660,828 B2 | 12/2003 | Thomas et al. | |
| 6,686,051 B1 | 2/2004 | Weinert et al. | |
| 6,727,344 B2 | 4/2004 | Weinert et al. | |
| 6,803,109 B2 | 10/2004 | Qiu et al. | |
| 6,825,316 B2 | 11/2004 | Malik et al. | |
| 6,849,762 B2 | 2/2005 | Fabian et al. | |
| 6,891,013 B1 | 5/2005 | Malik et al. | |
| 6,927,276 B2 | 8/2005 | Medsker et al. | |
| 6,962,966 B2 | 11/2005 | Medsker et al. | |
| 6,972,317 B2 | 12/2005 | Weinert et al. | |
| 6,998,460 B2 | 2/2006 | Malik et al. | |
| 7,022,801 B2 | 4/2006 | Medsker | |
| 7,087,710 B2 | 8/2006 | Medsker et al. | |
| 7,320,829 B2 | 1/2008 | Wright et al. | |
| 8,418,759 B2 | 4/2013 | Moore et al. | |
| 8,779,186 B2 | 7/2014 | Drysdale et al. | |
| 2001/0053866 A1 | 12/2001 | Denninger et al. | |
| 2003/0176721 A1 * | 9/2003 | Fabian | C07C 51/367 |
| | | | 558/415 |
| 2004/0002575 A1 | 1/2004 | Araki et al. | |
| 2004/0087759 A1 | 5/2004 | Malik et al. | |
| 2004/0152926 A1 * | 8/2004 | Mimura | C07C 29/124 |
| | | | 568/841 |
| 2004/0219350 A1 * | 11/2004 | Brown | C07C 41/03 |
| | | | 428/323 |
| 2007/0047099 A1 | 3/2007 | Clemens et al. | |
| 2008/0188673 A1 | 8/2008 | Lehmann et al. | |
| 2009/0143621 A1 | 6/2009 | Martin | |
| 2010/0279852 A1 | 11/2010 | Moloy | |
| 2010/0280278 A1 | 11/2010 | Moloy | |
| 2010/0280281 A1 | 11/2010 | Sweetman et al. | |
| 2011/0065892 A1 | 3/2011 | Ritter et al. | |
| 2012/0004470 A1 | 1/2012 | Matsumoto et al. | |
| 2012/0295134 A1 | 11/2012 | Wakabayashi et al. | |
| 2015/0065746 A1 | 3/2015 | Nair et al. | |
| 2015/0112095 A1 * | 4/2015 | Larichev | C07C 51/00 |
| | | | 560/184 |
| 2015/0361026 A1 | 12/2015 | Oomuro et al. | |
| 2018/0334417 A1 | 11/2018 | Greuel | |

FOREIGN PATENT DOCUMENTS

| | | | | |
|---|---|---|---|---|
| GB | 1233970 A * | 6/1971 | | D06M 15/568 |
| GB | 1 313 265 | 4/1973 | | |
| GB | 1352975 | 5/1974 | | |
| JP | 60-149533 A | 8/1985 | | |
| JP | 09-071547 A | 3/1997 | | |
| JP | 11-060530 A | 3/1999 | | |
| JP | 2011-505423 A | 2/2011 | | |
| WO | WO-9902498 A1 * | 1/1999 | | |
| WO | WO 2005/113644 A1 | 12/2005 | | |
| WO | WO 2009/073641 A1 | 6/2009 | | |
| WO | WO 2011/016492 A1 | 2/2011 | | |
| WO | WO-2011016492 A1 * | 2/2011 | | C07C 43/196 |
| WO | WO-2012107438 A1 * | 8/2012 | | C07C 41/01 |
| WO | WO-2012116196 A2 * | 8/2012 | | C07H 13/04 |

OTHER PUBLICATIONS

Sromek et al. "Synthesis and Evaluation of Fluorinated Aporphines: Potential Positron Emission Tomography Ligands for D2 Receptors", ACS Medicinal Chemistry Letters (2011), 2(3), 189-194 (Year: 2011).*
Collet et al. "Diastereoselective Synthesis of new O-alkylated and C-branched inositols and their corresponding fluoro analogues", Beilstein Journal of Organic Chemistry (2016), 12, 353-361 (Year: 2016).*
International Search Report and Written Opinion, in Counterpart Application PCT/US2018/033753, 17 pages, dated Sep. 21, 2018.
European Supplementary Search Report in Counter Part European Application No. 18802065.5 (dated Jan. 26, 2021), 11 pages.
Ameduri et al., "New Fluorinated Acrylic Monomers for the Surface Modification of UV-Curable Systems," Journal of Polymer Science: Part A: Polymer Chemistry, vol. 37 (1999) pp. 77-87.
Angeloff, C., JCPL, pp. 42-47, Aug. 2002.
Brunelle, D.J., et al., Editors, "Advances in Polycarbonates," 2005, ACS Symposium Series, pp. 8-21.

(56) References Cited

OTHER PUBLICATIONS

Guillaume, S. et al., editors, "Special Issue: Polycarbonates and Green Chemistry," including Xu, J., et al., Renaissance of Aliphatic Polycarbonates: New Techniques and Biomedical Applications, pp. 1-6, Journal of Applied Polymer Science, Mar. 5; 131(5) (2014).

Müller, B. et al., "Coatings Formulation: An International Textbook," $2^{nd}$ Revised Edition (2011), Hanover: Vincentz Network, pp. 98-159, 196-230 and 235-241.

Odian, G., "Principles of Polymerization," $4^{th}$ Edition, pp. 198-371 and 544-618 (2004), John Wiley & Sons, Inc.

Solomons, T.W. et al., "Organic Chemistry," $10^{th}$ Edition, John Wiley & Sons, Inc. pp. 230-267 and 518-521 (2011).

Streitwieser, A, et al., "Introduction to Organic Chemistry," 2nd Edition, Macmillan Publishing Co., Inc., pp. 237-239 (1981).

Japanese Office Action dated Dec. 21, 2021 (received by applicant Dec. 27, 2021) and Translation, 19 pages.

\* cited by examiner

METHODS FOR MAKING FUNCTIONALIZED FLUORINATED MONOMERS, FLUORINATED MONOMERS, AND COMPOSITIONS FOR MAKING THE SAME

CROSS-REFERENCE TO RELATED APPLICATIONS

This application claims the benefit under 35 U.S.C. § 119(e) of U.S. Provisional Patent Application No. 62/560,641, filed Sep. 19, 2017, entitled, "Methods for Forming Functionalized Fluorinated Monomers, Fluorinated Monomers, and Compositions for Forming the Same," and of U.S. Provisional Patent Application No. 62/508,835, filed May 19, 2017, also entitled, "Methods for Forming Functionalized Fluorinated Monomers, Fluorinated Monomers, and Compositions for Forming the Same," the entire disclosures of which are incorporated herein by reference.

BACKGROUND OF THE INVENTION

Field of the Invention

The invention relates to methods for making functionalized fluorinated monomers that can be used to produce fluoropolymers, such as fluorine-containing polyesters, polycarbonates, polyurethanes, polyethers, and polyureas, among others. Such fluorine-containing polymers are useful for various applications such as for use as lubricant additives and coatings with improved surface properties, such as graffiti-resistance, stain-resistance, self-cleaning ability, hardness, and transparency.

Description of Related Art

Bulk fluorinated materials are often used to improve the surface properties of polymer-based systems, such as coatings. Bulk fluorinated materials, such as vinylidine fluoride (VDF)-containing polymers and tetrafluoroethylene (TFE)-containing polymers are conventionally used for such applications. However, bulk fluorinated materials are expensive and may lack desirable physical properties, such as hardness, abrasion-resistance, and transparency.

Due to the deficiencies and drawbacks related to the use of bulk fluorinated materials, fluorinated surfactants have also been used as coating additives. The use of fluorinated surfactants allows for coatings to be produced in a conventional manner using conventional chemistries, wherein the fluorinated surfactants are added to the traditional coatings and resins to provide the desired surface property improvements. However, the beneficial effects of the fluorinated surfactants are only temporary, as the fluorinated surfactant may be washed away or eroded over time and thus the surface properties may be lost or degraded over extended periods.

U.S. Pat. No. 6,383,651 discloses the synthesis of polyesters containing blocks of fluorinated oxetane prepolymers, such as the fluorinated oxetane prepolymers disclosed in U.S. Pat. No. 5,650,483. The '651 patent aims to provide a polyester resin having low surface energy, high hydrophobicity, and a low coefficient of friction, which can result in improved stain- and abrasion-resistance. Such polyester resins are made by reacting the polyoxetane with a dicarboxylic acid or anhydride and incorporating the resulting carboxylic acid terminated material into the polyester.

Various other methods have been disclosed for improving surface properties in polymer based systems. U.S. Pat. No. 4,595,632 discloses the grafting of fluorine-containing groups onto the surface of articles derived from polymers, such as natural rubber by epoxidizing the surface of a substrate and then reacting the epoxide groups on the surface with a fluorine-containing reagent.

U.S. Pat. No. 6,803,109 discloses fluorine-containing urethane oligomers having fluorine-containing repeating units and terminal groups derived from fluorinated alcohols. U.S. Pat. No. 8,418,759 discloses the synthesis and use of fluorine-containing polyether polymers for oilfield applications by ring opening polymerization and copolymerization of fluorine-containing oxiranes. U.S. Pat. No. 8,779,186 provides synthesis of fluorinated ethers of aromatic acids and di esters thereof for use as monomers and surfactants. Further, U.S. Patent Application Publication No. 2015/0361026 provides methods for the synthesis of fluorine-containing hydroxyaldehyde, propanediol, and alcohol monomers for use as raw materials for photoresists.

While the method of incorporating fluorinated oxetane-based polyether blocks into polyesters and other polymers may provide some benefits to the surface properties thereof, this method has various limitations. Specifically, the presence of partially fluorinated polyether domains in the polymer results in a hazy or translucent appearance even at low concentrations. Further, such polymers have low surface hardness in coatings and in other materials derived from the polymers. This is because the soft, partially fluorinated polyether blocks have a tendency to migrate to the surface.

As a result, there remains a need to provide stable and long-term improvement in the surface properties of polymer-containing systems while maintaining physical properties, such as hardness. There is also a need in the art for minimizing the amount of fluorine-containing monomers required to make polymers suitable for polymer systems that provide modified surface properties. Such polymers would desirably further exhibit improved transparency, hardness, and abrasion-resistance and would be relatively inexpensive compared to bulk fluorinated polymers. There is also a need in the art for inexpensively made fluorinated monomers which would be used to make a variety of polymers, such as polyesters, polycarbonates, polyurethanes, polyethers, and polyureas, among others that can be used in end applications in various industries.

BRIEF SUMMARY OF THE INVENTION

The present invention relates to methods for making functionalized fluorinated monomers useful for making fluorine-containing polymers and oligomers that can be used in coatings and as additives to lubricant compositions for metalworking and automotive applications, such as motor and gear oils, among various other end applications. These functionalized fluorinated monomers are useful in producing various oligomers and polymers, examples of which include fluorine-containing polyester polyols, polycarbonate polyols, and polyaspartic esters, among others. The resulting fluorine-containing oligomers and polymers provide improved surface properties when incorporated into coatings, such as graffiti-resistance, stain-resistance, self-cleaning ability, hydrophobicity, and transparency. Improved transparency is particularly useful in coatings for glass and other substrates where transparency is desirable.

The present invention includes methods for producing functionalized fluorinated monomers by reacting at least one fluorinated nucleophilic reactant(s) having functional reactant group(s) with at least one compound(s) comprising at least one epoxide group.

In one embodiment, the invention includes a method of making functionalized fluorinated monomers by reacting one or more fluorinated alcohol(s) with one or more cyclic carboxylic acid anhydride(s). Additionally, methods are also included herein for making functionalized fluorinated monomers that involve reacting fluorinated mesylates, tosylates, or triflates with amines or polyamines, alcohols, polyols, phenols or polyphenols; or alkoxide intermediates or phenoxide intermediates. Also described are methods for making functionalized fluorinated monomers that involve reacting at least one fluorinated alkyl halide(s) with one or more amine(s) or polyamine(s). Further described are methods for making functionalized fluorinated monomers that involve reacting one or more fluorinated alcohols with one or more alkyl halide(s) having one or more functional group(s) thereon. In another embodiment, the invention includes functionalized fluorinated monomers produced by these methods and compositions for making functionalized fluorinated monomers. Also included are methods for making chain-extended fluorinated monomers that involve reacting at least one monomer(s) of the present invention with one or more cyclic reactant(s), such as cyclic carboxylic acid anhydrides, cyclic esters, cyclic carbonates, or cyclic ethers, or by reacting unsaturated functionalized fluorinated monomers with polyamines.

The present invention further relates to methods for making polymers and oligomers from the functionalized fluorinated monomers produced by any of the methods recited herein and to the polymers produced thereby. Hydroxy-, carboxylic acid- and carboxylic ester-functional fluorinated monomers of the present invention can be used to synthesize fluorinated polyesters. Further, hydroxy-functional fluorinated monomers can be used to synthesize fluorinated polycarbonates and polyurethanes, as well as polyethers and polyesters via ring-opening polymerization. The amino-functional fluorinated monomers can be used to synthesize fluorinated polyureas and as curatives for epoxy resin systems. Further, unsaturated fluorinated monomers can be incorporated into free radical polymerizations to synthesize various useful fluorinated polymers.

In one embodiment, the invention relates to a method for making a functionalized fluorinated monomer, comprising reacting at least one fluorinated nucleophilic reactant(s) with at least one compound(s) comprising at least one epoxide group to form a functionalized fluorinated monomer having at least one hydroxyl group. The fluorinated nucleophilic reactant(s) is/are preferably selected from the group of a fluorinated alcohol, a fluorinated carboxylic acid, a fluorinated organic acid anhydride, a fluorinated amine, a fluorinated thiol, a fluorinated amide, a fluorinated sulfonamide, and combinations thereof. In some embodiments, the fluorinated nucleophilic reactant may be a combination, such as a mixture, of two or more such fluorinated nucleophilic reactants. In one embodiment, the at least one compound comprising an epoxide group is selected from the group of 1,4-butanediol diglycidyl ether; 1,4-cyclohexanedimethanol diglycidyl ether; 1-6-hexanediol diglycidyl ether; 3,4-epoxycyclohexylmethyl-3,4-epoxycyclohexanecarboxylate; bis(3,4-epoxycyclohexylmethyl)adipate; trimethylolpropane triglycidyl ether; sorbitol polyglycidyl ether; and pentaerythritol tetraglycidyl ether.

In embodiments wherein the at least one fluorinated nucleophilic reactant is a fluorinated alcohol, the fluorinated alcohol may be a phenol, diol, or polyol. In a preferred embodiment, the at least one fluorinated nucleophilic reactant is a fluorinated alcohol selected from the group of 2,2,2-trifluoroethanol, 2,2,3,3,3-pentalluoro-1-propanol; 1,1,1,3,3,3-hexafluoro-2-propanol, 4-hydroxyphenylsulfur pentafluoride; 2-perfluoropropoxy-2,3,3,3-tetrafluoropropanol; and 3,3,4,4,5,5,6,6,7,7,8,8-tridecafluoro-1-octanol.

If the fluorinated alcohol is a fluorinated diol or polyol, the compound comprising at least one epoxide group preferably comprises only one epoxide group such that the reaction yields a functionalized fluorinated monomer that is a diol or polyol having at least one ether linkage.

In one embodiment, the reaction of the fluorinated alcohol and at least one compound comprising at least one epoxide group may take place in the presence of a base catalyst. Examples of such catalysts include potassium hydroxide, sodium hydride, sodium methoxide, trimethylamine, and diazabicycloundecene (DBU). The functionalized fluorinated monomer in such an embodiment may have at least one hydroxyl group that is a secondary hydroxyl group or groups. In another embodiment, and when the fluorinated nucleophilic reactant is a fluorinated alcohol, the functionalized fluorinated monomer has a structure according to formula (I):

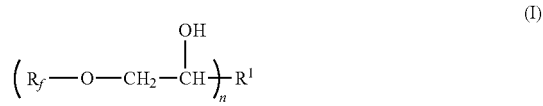

(I)

wherein:
$R_f$ is a partially or fully fluorinated, branched or unbranched, substituted or unsubstituted alkyl group having one to about eighteen carbon atoms, and having 0 to 6 ether linkages, and when substituted includes a group selected from an aromatic group, a sulfur pentafluoride group, and a halogen atom, or a combination thereof; or is a partially or fully fluorinated, substituted or unsubstituted aryl group, that when substituted includes a sulfur pentafluoride group, a halogen atom, or a combination thereof;
$R^1$ is hydrogen, $R_f$, or a saturated or unsaturated, branched or unbranched, substituted or unsubstituted alkyl group, cyclic alkyl group or heterocyclic group having 1 to about 24 carbon atoms, wherein when $R^1$ is an alkyl group, a cyclic alkyl group, or a heterocyclic group, $R^1$ comprises 0 to 6 ether linkages, ester linkages, or aryl groups; and
n is 1 to about 4.

When $R^1$ is substituted, $R^1$ may have one or more functional groups selected from the group of a hydroxyl group, a halogen, an epoxide, a carboxylic acid, a carboxylic acid ester, a carboxylate salt, an amine, and a thiol.

In a further embodiment, the invention includes a functionalized fluorinated monomer according to the disclosure herein wherein the functionalized fluorinated monomer is a fluorinated polyol.

Alternately, the fluorinated nucleophilic reactant may be a fluorinated alcohol, and the reaction of the fluorinated alcohol and the compound comprising at least one epoxide group may take place in the presence of an acid catalyst. Examples of such a catalyst include hydrochloric acid, sulfuric acid, or methanesulfonic acid. In such an embodiment, one of the at least one hydroxyl group of the functionalized fluorinated monomer is a primary hydroxyl group. In an embodiment where the fluorinated nucleophilic reactant is a fluorinated alcohol, the functionalized fluorinated monomer has a structure according to formula (II):

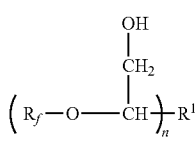

wherein:

$R_f$ is a partially or fully fluorinated, branched or unbranched, substituted or unsubstituted alkyl group having one to about eighteen carbon atoms, and having 0 to 6 ether linkages, and when substituted includes a group selected from an aromatic group, a sulfur pentafluoride group, and a halogen atom, or a combination thereof; or is a partially or fully fluorinated, substituted or unsubstituted aryl group, that when substituted includes a sulfur pentafluoride group, a halogen atom, or a combination thereof;

$R^1$ is hydrogen, $R_f$, or a saturated or unsaturated, branched or unbranched, substituted or unsubstituted alkyl group, cyclic alkyl group or heterocyclic group having 1 to about 24 carbon atoms, wherein when $R^1$ is an alkyl group, a cyclic alkyl group, or a heterocyclic group, $R^1$ comprises 0 to 6 ether linkages, ester linkages, or aryl groups; and n is 1 to about 4.

Further, when $R^1$ is substituted, $R^1$ may have one or more functional groups selected from the group of a hydroxyl group, a halogen, an epoxide, a carboxylic acid, a carboxylic acid ester, a carboxylate salt, an amine, and a thiol.

In embodiments wherein the at least one fluorinated nucleophilic reactant is a carboxylic acid, the functionalized fluorinated monomer may comprise at least one hydroxyl group and an ester linkage, and preferably, the functionalized fluorinated monomer has a structure according to formula (III):

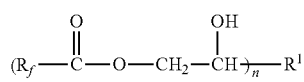

wherein:

$R_f$ is a partially or fully fluorinated, branched or unbranched, substituted or unsubstituted alkyl group having one to about eighteen carbon atoms, and having 0 to 6 ether linkages, and when substituted includes a group selected from an aromatic group, a sulfur pentafluoride group, and a halogen atom, or a combination thereof; or is a partially or fully fluorinated, substituted or unsubstituted aryl group, that when substituted includes a sulfur pentafluoride group, a halogen atom, or a combination thereof;

$R^1$ is hydrogen, $R_f$, or a saturated or unsaturated, branched or unbranched, substituted or unsubstituted alkyl group, cyclic alkyl group or heterocyclic group having 1 to about 24 carbon atoms, wherein when $R^1$ is an alkyl group, a cyclic alkyl group, or a heterocyclic group, $R^1$ comprises 0 to 6 ether linkages, ester linkages, or aryl groups; and n is 1 to about 4.

Further, when $R^1$ is substituted, $R^1$ may have one or more functional groups selected from the group of a hydroxyl group, a halogen, an epoxide, a carboxylic acid, a carboxylic acid ester, a carboxylate salt, an amine, and a thiol.

In one embodiment, the fluorinated nucleophilic reactant is a fluorinated carboxylic acid preferably selected from the group of trifluoroacetic acid; pentafluoropropionic acid; 2,2-bis(trifluoromethyl)propionic acid; 4,4,4-trifluorobutyric acid; heptafluorobutyric acid; 4,4,5,5,6,6,6-heptafluorohexanoic acid; 4-pentafluorothiobenzoic acid; and 3,5-bis(trifluoromethyl)benzoic acid.

In another embodiment, the fluorinated nucleophilic reactant is a fluorinated carboxylic acid that is a fluorinated di carboxylic acid, and the compound comprising at least one epoxide group may have only one epoxide group, such that the functionalized fluorinated monomer is a fluorinated diol having an ester linkage.

In one embodiment, the at least one fluorinated nucleophilic reactant is a fluorinated amine, and the functionalized fluorinated monomer comprises an amine group. Preferably, the functionalized fluorinated monomer has a structure according to formula (IV):

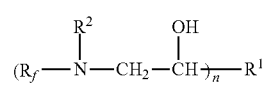

wherein:

$R_f$ is a partially or fully fluorinated, branched or unbranched, substituted or unsubstituted alkyl group having one to about eighteen carbon atoms, and having 0 to 6 ether linkages, and when substituted includes a group selected from an aromatic group, a sulfur pentafluoride group, and a halogen atom, or a combination thereof; or is a partially or fully fluorinated, substituted or unsubstituted aryl group, that when substituted includes a sulfur pentafluoride group, a halogen atom, or a combination thereof;

$R^1$ is hydrogen, $R_f$, or a saturated or unsaturated, branched or unbranched, substituted or unsubstituted alkyl group, cyclic alkyl group or heterocyclic group having 1 to about 24 carbon atoms, wherein when $R^1$ is an alkyl group, a cyclic alkyl group, or a heterocyclic group, $R^1$ comprises 0 to 6 ether linkages, ester linkages, or aryl groups; and wherein n is 1 to about 4;

$R^2$ is hydrogen, $R_f$, or a saturated, branched or unbranched, substituted or unsubstituted alkyl group having one to about six carbon atoms; and n is 1 to about 4.

Further, when $R^1$ and/or $R^2$ are substituted, $R^1$ and/or $R^2$ may have one or more functional groups selected from the group of a hydroxyl group, a halogen, an epoxide, a carboxylic acid, a carboxylic acid ester, a carboxylate salt, an amine, and a thiol.

In another embodiment, the at least one fluorinated nucleophilic reactant may be a fluorinated amide, and the functionalized fluorinated monomer may include an amide group. Such a reaction may preferably take place in the presence of a base catalyst, including, for example, potassium hydroxide, trimethylamine, or DBU. In a further embodiment, the fluorinated amide is preferably 2,2,2-trifluoroacetamide. When the fluorinated nucleophilic reactant is a fluorinated amide, the functionalized fluorinated monomer may also have a structure according to formula (V):

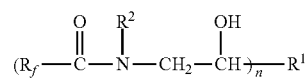

wherein:
$R_f$ is a partially or fully fluorinated, branched or unbranched, substituted or unsubstituted alkyl group having one to about eighteen carbon atoms, and having 0 to 6 ether linkages, and when substituted includes a group selected from an aromatic group, a sulfur pentafluoride group, and a halogen atom, or a combination thereof; or is a partially or fully fluorinated, substituted or unsubstituted aryl group, that when substituted includes a sulfur pentafluoride group, a halogen atom, or a combination thereof;
$R^1$ is hydrogen, $R_f$, or a saturated or unsaturated, branched or unbranched, substituted or unsubstituted alkyl group, cyclic alkyl group or heterocyclic group having 1 to about 24 carbon atoms, wherein when $R^1$ is an alkyl group, a cyclic alkyl group, or a heterocyclic group, $R^1$ comprises 0 to 6 ether linkages, ester linkages, or aryl groups;
$R^2$ is hydrogen, $R_f$, or a saturated, branched or unbranched, substituted or unsubstituted alkyl group having one to about six carbon atoms; and
n is 1 to about 4.

Further, when $R^1$ and/or $R^2$ are substituted, $R^1$ and/or $R^2$ may have one or more functional groups selected from the group of a hydroxyl group, a halogen, an epoxide, a carboxylic acid, a carboxylic acid ester, a carboxylate salt, an amine, and a thiol.

In a further embodiment, the fluorinated nucleophilic reactant is a sulfonamide, and the functionalized fluorinated monomer has a sulfonamide linkage. Preferably, the reaction takes place in the presence of a base catalyst, such as potassium hydroxide, trimethylamine, or DBU. Preferably, when the fluorinated nucleophilic reactant is a sulfonamide, the sulfonamide is 2,2,2-trifluoroethanesufonamide. In another such embodiment, when the nucleophilic reactant is a sulfonamide, the functionalized fluorinated monomer has a structure according to formula (VI):

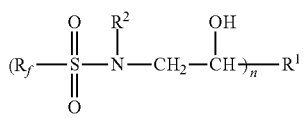
(VI)

wherein:
$R_f$ is a partially or fully fluorinated, branched or unbranched, substituted or unsubstituted alkyl group having one to about eighteen carbon atoms, and having 0 to 6 ether linkages, and when substituted includes a group selected from an aromatic group, a sulfur pentafluoride group, and a halogen atom, or a combination thereof; or is a partially or fully fluorinated, substituted or unsubstituted aryl group, that when substituted includes a sulfur pentafluoride group, a halogen atom, or a combination thereof;
$R^1$ is hydrogen, $R_f$, or a saturated or unsaturated, branched or unbranched, substituted or unsubstituted alkyl group, cyclic alkyl group or heterocyclic group having 1 to about 24 carbon atoms, wherein when $R^1$ is an alkyl group, a cyclic alkyl group, or a heterocyclic group, $R^1$ comprises 0 to 6 ether linkages, ester linkages, or aryl groups;
$R^2$ is hydrogen, $R_f$, or a saturated, branched or unbranched, substituted or unsubstituted alkyl group having one to about six carbon atoms; and
n is 1 to about 4.

Further, when $R^1$ and/or Fe are substituted, $R^1$ and/or $R^2$ may have one or more functional groups selected from the group of a hydroxyl group, a halogen, an epoxide, a carboxylic acid, a carboxylic acid ester, a carboxylate salt, an amine, and a thiol.

The fluorinated nucleophilic reactant may also be a fluorinated thiol, in which case the functionalized fluorinated monomer has a thioether linkage. Preferably, the functionalized fluorinated monomer has a structure according to formula (VII):

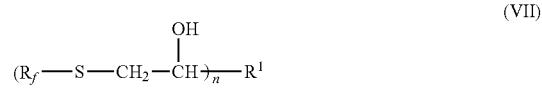
(VII)

wherein:
$R_f$ is a partially or fully fluorinated, branched or unbranched, substituted or unsubstituted alkyl group having one to about eighteen carbon atoms, and having 0 to 6 ether linkages, and when substituted includes a group selected from an aromatic group, a sulfur pentafluoride group, and a halogen atom, or a combination thereof; or is a partially or fully fluorinated, substituted or unsubstituted aryl group, that when substituted includes a sulfur pentafluoride group, a halogen atom, or a combination thereof;
$R^1$ is hydrogen, $R_f$, or a saturated or unsaturated, branched or unbranched, substituted or unsubstituted alkyl group, cyclic alkyl group or heterocyclic group having 1 to about 24 carbon atoms, wherein when $R^1$ is an alkyl group, a cyclic alkyl group, or a heterocyclic group, $R^1$ comprises 0 to 6 ether linkages, ester linkages, or aryl groups; and
n is 1 to about 4.

Further, when $R^1$ is substituted, $R^1$ may have one or more functional groups selected from the group of a hydroxyl group, a halogen, an epoxide, a carboxylic acid, a carboxylic acid ester, a carboxylate salt, an amine, and a thiol.

In another embodiment, the fluorinated nucleophilic reactant is a fluorinated organic acid anhydride, and the functionalized fluorinated monomer comprises at least one hydroxyl group and an ester linkage. Preferably, the functionalized fluorinated monomer has a structure according to formula (III):

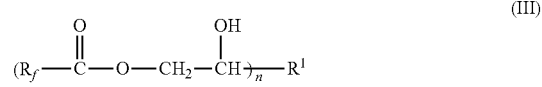
(III)

wherein:
$R_f$ is a partially or fully fluorinated, branched or unbranched, substituted or unsubstituted alkyl group having one to about eighteen carbon atoms, and having 0 to 6 ether linkages, and when substituted includes a group selected from an aromatic group, a sulfur pentafluoride group, and a halogen atom, or a combination thereof; or is a partially or fully fluorinated, substituted or unsubstituted aryl group, that when substituted includes a sulfur pentafluoride group, a halogen atom, or a combination thereof;
$R^1$ is hydrogen, $R_f$, or a saturated or unsaturated, branched or unbranched, substituted or unsubstituted alkyl group, cyclic alkyl group or heterocyclic group having 1 to about 24 carbon atoms, wherein when $R^1$ is an alkyl group, a cyclic alkyl group, or a heterocyclic group, $R^1$ comprises 0 to 6 ether linkages, ester linkages, or aryl groups; and
n is 1 to about 4.

Further, when $R^1$ is substituted, $R^1$ may have one or more functional groups selected from the group of a hydroxyl group, a halogen, an epoxide, a carboxylic acid, a carboxylic acid ester, a carboxylate salt, an amine, and a thiol.

The present invention further relates to functionalized fluorinated monomers made by the reaction of a fluorinated nucleophilic reactant with a compound comprising at least one epoxide group. The fluorinated nucleophilic reactant may be any of a fluorinated alcohol, a fluorinated carboxylic acid, a fluorinated organic acid anhydride, a fluorinated amine, a fluorinated amide, a fluorinated sulfonamide, a fluorinated thiol, and combinations thereof, for example, the fluorinated nucleophilic reactant may be a mixture of two such reactants.

The present invention also relates to compositions for making functionalized fluorinated monomers, wherein the composition comprises at least one fluorinated nucleophilic reactant and at least one compound comprising at least one epoxide group. The fluorinated nucleophilic reactant may be any one of a fluorinated alcohol, a fluorinated carboxylic acid, a fluorinated organic acid anhydride, a fluorinated amine, a fluorinated amide, a fluorinated sulfonamide, a fluorinated thiol or may be combinations thereof, including a mixture of two such reactants.

The present invention further relates to a method of making polymers or oligomers comprising polymerizing a functionalized fluorinated monomer having at least one hydroxyl group, preferably using a method for making such functionalized fluorinated monomer of the invention as described herein, to form a fluorinated polyester via condensation or ring opening polymerization.

Further included in the invention is a method of making polymers or oligomers, comprising polymerizing a functionalized fluorinated monomer having at least one hydroxyl group, preferably using a method for making such functionalized fluorinated monomer of the invention as described herein, to form a fluorinated polycarbonate via condensation polymerization or ring opening polymerization.

In another embodiment of the present invention, the present invention provides a method for making a functionalized fluorinated monomer, comprising reacting at least one first reactant selected from a fluorinated mesylate, a fluorinated tosylate, and a fluorinated trifluoromethanesulfonate ("triflate"), with at least one second reactant selected from an amine or polyamine; an alcohol, polyol, phenol or polyphenol; and an alkoxide intermediate or phenoxide intermediate, to form a functionalized fluorinated monomer.

When the at least one second reactant in this embodiment is an amine or a polyamine, the functionalized fluorinated monomer made by the reaction is a fluorinated amine or a fluorinated polyamine, respectively. Preferably, the functionalized fluorinated monomer is produced by a reaction according to formula (VIII):

(VIII)

wherein:
A is a functional group corresponding to a mesylate, tosylate or triflate;
$R_f$ is a partially or fully fluorinated, branched or unbranched, substituted or unsubstituted alkyl group having one to about eighteen carbon atoms, and having 0 to 6 ether linkages, and when substituted includes a group selected from an aromatic group, a sulfur pentafluoride group, and a halogen atom, or a combination thereof; or is a partially or fully fluorinated, substituted or unsubstituted aryl group, that when substituted includes a sulfur pentafluoride group, a halogen atom, or a combination thereof;

$R^1$ is hydrogen, $R_f$, or a saturated or unsaturated, branched or unbranched, substituted or unsubstituted alkyl group, cyclic alkyl group or heterocyclic group having one to about twelve carbon atoms, wherein when $R^1$ is an alkyl group, a cyclic alkyl group, or a heterocyclic group, $R^1$ comprises 0 to 6 ether linkages, ester linkages, or aryl groups;
$R^2$ is hydrogen, $R_f$, or a saturated, branched or unbranched, substituted or unsubstituted alkyl group of one to about six carbon atoms; and
n is 1 to about 6.

Further, when $R^1$ and/or $R^2$ are substituted, and/or may have one or more functional groups selected from the group of a hydroxyl group, a halogen, a carboxylic acid, a carboxylic acid ester, a carboxylate salt, an amine, and a thiol.

In the above embodiment, wherein when the at least one second reactant is an alkoxide intermediate or a phenoxide intermediate, the functionalized fluorinated monomer is a fluorinated ether. Preferably, the functionalized fluorinated monomer in this embodiment is made by a reaction according to formula (IX):

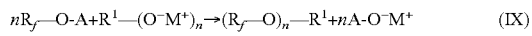
(IX)

wherein:
A is a functional group corresponding to a mesylate, tosylate or triflate;
$M^+$ is a counterion derived from the base used to generate the alkoxide or phenoxide intermediate;
$R_f$ is a partially or fully fluorinated, branched or unbranched, substituted or unsubstituted alkyl group having one to about eighteen carbon atoms, and having 0 to 6 ether linkages, and when substituted includes a group selected from an aromatic group, a sulfur pentafluoride group, and a halogen atom, or a combination thereof; or is a partially or fully fluorinated, substituted or unsubstituted aryl group, that when substituted includes a sulfur pentafluoride group, a halogen atom, or a combination thereof;
$R^1$ is hydrogen, $R_f$, or a saturated or unsaturated, branched or unbranched, substituted or unsubstituted alkyl group, cyclic alkyl group or heterocyclic group having one to about twelve carbon atoms, wherein when $R^1$ is an alkyl group, a cyclic alkyl group, or a heterocyclic group, $R^1$ comprises 0 to 6 ether linkages, ester linkages, or aryl groups; and
n is 1 to about 6.

Further, when $R^1$ is substituted, $R^1$ may have one or more functional groups selected from the group of a hydroxyl group, a halogen, a carboxylic acid, a carboxylic acid ester, a carboxylate salt, an amine, and a thiol.

The present invention further provides functionalized fluorinated monomers made by reacting at least one first reactant selected from a fluorinated mesylate, a fluorinated tosylate, and a fluorinated triflate, with at least one second reactant selected from an amine or a polyamine; an alcohol, a polyol, a phenol or a polyphenol; and an alkoxide intermediate or a phenoxide intermediate.

Further provided are compositions for making functionalized fluorinated monomers, comprising a first reactant selected from at least one of a fluorinated mesylate, a fluorinated tosylate, a fluorinated triflate, or a combination thereof, and at least one second reactant selected from an amine or a polyamine; an alcohol, a polyol, a phenol or a polyphenol; and an alkoxide intermediate or a phenoxide intermediate.

In another embodiment of the present invention, a method is provided for making a functionalized fluorinated monomer, comprising reacting at least one fluorinated alkyl or aryl halide with an amine to form an amino-functionalized fluorinated monomer. The fluorinated alkyl or aryl halide is preferably an iodide. Further, the amine is preferably a primary or secondary amine. In some embodiments, the amine may be a polyamine. The functionalized fluorinated monomer is made by a reaction according to formula (X):

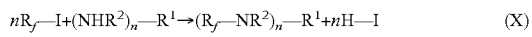
$$nR_f-I+(NHR^2)_n-R^1 \rightarrow (R_f-NR^2)_n-R^1+nH-I \quad (X)$$

wherein:
$R_f$ is a partially or fully fluorinated, branched or unbranched, substituted or unsubstituted alkyl group having one to about eighteen carbon atoms, and having 0 to 6 ether linkages, and when substituted includes a group selected from an aromatic group, a sulfur pentafluoride group, and a halogen atom, or a combination thereof; or is a partially or felly fluorinated, substituted or unsubstituted aryl group, that when substituted includes a sulfur pentafluoride group, a halogen atom, or a combination thereof;
$R^1$ is hydrogen, $R_f$, or a saturated or unsaturated, branched or unbranched, substituted or unsubstituted alkyl group, cyclic alkyl group or heterocyclic group having one to about twelve carbon atoms, wherein when is an alkyl group, a cyclic alkyl group, or a heterocyclic group, $R^1$ comprises 0 to 6 ether linkages, ester linkages, or aryl groups;
$R^2$ is hydrogen, $R_f$; or a saturated, branched or unbranched, substituted or unsubstituted alkyl group of one to about six carbon atoms; and
n is 1 to about 6.

Further, when $R^1$ and/or $R^2$ are substituted, $R^1$ and/or $R^2$ may have one or more functional groups selected from the group of a hydroxyl group, a halogen, a carboxylic acid, a carboxylic acid ester, a carboxylate salt, an amine, and a thiol.

The present invention further provides functionalized fluorinated monomers made by reacting one or more fluorinated alkyl or aryl halides with one or more amines to form an amino-functionalized fluorinated monomer. Also provided are compositions for making functionalized fluorinated monomers comprising one or more fluorinated or aryl halides, preferably a fluorinated alkyl or aryl iodide, and one or more amines or polyamines.

Another embodiment of the present invention provides a method for making a functionalized fluorinated monomer comprising reacting one or more fluorinated alcohols with one or more alkyl or aryl halides having at least one functional group, in the presence of a base catalyst to make a functionalized fluorinated monomer having an ether linkage and at least one functional group derived from the alkyl or aryl halide molecule. Reaction of the at least one fluorinated alcohol and the alkyl or aryl halide molecule having at least one functional group preferably takes place via nucleophilic substitution. The alkyl or an halide molecule is preferably a primary or secondary alkyl halide. In one embodiment, the at least one functional group of the alkyl or aryl halide molecule is selected from the group of a hydroxyl group, a carboxylic acid, a carboxylic acid ester, a carboxylate salt, an amine, and a thiol. The base catalyst is preferably an alkoxide, a hydride or a hydroxide of an alkali or alkaline earth metal.

In a preferred embodiment of this method, the functionalized fluorinated monomer is made by and the reaction takes place according to the following formula (XI):

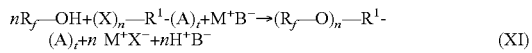
$$nR_f-OH+(X)_n-R^1-(A)_t+M^+B^- \rightarrow (R_f-O)_n-R^1-(A)_t+n\,M^+X^-+nH^+B^- \quad (XI)$$

wherein:
X is a halogen;
$R_f$ is a partially or fully fluorinated, branched or unbranched, substituted or unsubstituted alkyl group having one to about eighteen carbon atoms, and having 0 to 6 ether linkages, and when substituted includes a group selected from an aromatic group, a sulfur pentafluoride group, and a halogen atom, or a combination thereof; or is a partially or fully fluorinated, substituted or unsubstituted aryl group, that when substituted includes a sulfur pentafluoride group, a halogen atom, or a combination thereof;
A is a functional group selected from a halogen, hydroxyl, epoxide, carboxylic acid, carboxylic acid ester, carboxylate salt, amine, and thiol;
$R^1$ is hydrogen, $R_f$, or a saturated or unsaturated, branched or unbranched, substituted or unsubstituted alkyl group, cyclic alkyl group, or heterocyclic group having one to about twelve carbon atoms, wherein when $R^1$ is an alkyl group, a cyclic alkyl group or a heterocyclic group, $R^1$ comprises 0 to 6 ether linkages, ester linkages, or aryl groups; and
$M^+$ is a metal or other cation;
$B^-$ is a base;
t is 1 to 4; and
n is 1 to about 6.

The present invention further provides a functionalized fluorinated monomer made by the method of reacting at least one fluorinated alcohol with an alkyl or aryl halide molecule having at least one functional group in the presence of a base catalyst. Further provided are compositions for making a functionalized fluorinated monomer, comprising at least one fluorinated alcohol and an alkyl or aryl halide molecule having at least one functional group.

The invention further includes a method of making a chain extended fluorinated monomer, comprising reacting a functionalized fluorinated monomer having at least one hydroxyl group, made by the method of reacting at least one fluorinated alcohol with an alkyl or aryl halide molecule having at least one functional group in the presence of a base catalyst as noted above, with a cyclic reactant selected from the group of a cyclic carboxylic anhydride, a cyclic ether, a cyclic carbonate, and a cyclic ester to form a chain extended fluorinated monomer or a chain-extended fluorinated oligomer.

In such an embodiment, the functionalized fluorinated monomer is preferably a fluorinated diol having at least one ether linkage and the chain-extended fluorinated monomer is a fluorinated dicarboxylic acid. Also included are chain-extended fluorinated monomers made by this method. Further included is a method for making a polymer or oligomer, comprising polymerizing a chain extended functionalized fluorinated monomer having at least one carboxylic acid group formed by the method of this embodiment via condensation polymerization to form a fluorinated polyester. In another such embodiment, the cyclic reactant is preferably a cyclic ether selected from the group of propylene oxide, glycidol, epichlorohydrin, butyl glycidyl ether, and 2-ethylhexyl glycidyl ether. The cyclic reactant may also be a cyclic ester selected from the group of L-lactide, glycolide, and ε-caprolactone and most preferably ε-caprolactone. The cyclic reactant may also be a cyclic carbonate selected from the group of ethylene carbonate, propylene carbonate, and trimethylene carbonate, and of which the reactant is preferably trimethylene carbonate. The reactant may also be a cyclic carboxylic anhydride selected from the group of succinic anhydride, maleic anhydride, itaconic anhydride, aconitic anhydride, phthalic anhydride, hexahydrophthalic anhydride, trimellitic anhydride, and 1,2,4-cyclohexanetricarboxylic anhydride.

Also included is a method for making a polymer or oligomer, comprising reacting a functionalized fluorinated monomer having a hydroxyl group with a cyclic ester, cyclic carbonate, or a cyclic ether via ring opening polymerization to form a fluorine-containing polyester polyol, a fluorine-containing polycarbonate polyol or a fluorine-containing polyether polyol, respectively, wherein the functionalized fluorinated monomer used in the method is either (i) made by reacting at least one fluorinated alcohol with an alkyl or aryl halide molecule having at least one functional group in the presence of a base catalyst to make a functionalized fluorinated monomer having an ether linkage and the at least one functional group of the alkyl or aryl halide or GO is a chain extended fluorinated monomer made by reacting a functionalized fluorinated monomer having at least one hydroxyl group made by reacting (a) at least one fluorinated alcohol with an alkyl or aryl halide molecule having at least one functional group in the presence of a base catalyst to make a functionalized fluorinated monomer having an ether linkage and the at least one functional group of the alkyl or aryl halide with (b) a cyclic reactant selected from the group of a cyclic carboxylic anhydride, a cyclic ether, a cyclic carbonate, and a cyclic ester.

In another embodiment according to the present invention, the invention includes a method of making a functionalized fluorinated monomer comprising reacting at least one fluorinated alcohol with a cyclic carboxylic acid anhydride to form a functionalized fluorinated monomer comprising a carboxylic acid group and an ester linkage. This reaction preferably takes place at a temperature of at least about 80° C. In one embodiment, the functionalized fluorinated monomer resulting from the method has formula (XII):

(XII)

wherein:
$R_f$ is a partially or fully fluorinated, branched or unbranched, substituted or unsubstituted alkyl group having one to about eighteen carbon atoms, and having 0 to 6 ether linkages, and when substituted includes a group selected from an aromatic group, a sulfur pentafluoride group, and a halogen atom, and a combination thereof; or is a partially or fully fluorinated, substituted or unsubstituted aryl group, that when substituted includes a sulfur pentafluoride group, a halogen atom, or a combination thereof; and $R^3$ is a saturated or unsaturated, branched or unbranched, substituted or unsubstituted alkyl group, cyclic alkyl group, aryl group, or heterocyclic group having two to about eighteen carbon atoms, and when $R^3$ is substituted, $R^3$ includes one or more functional groups selected from the group of a halogen, a carboxylic acid, carboxylic acid ester, and a carboxylic acid anhydride.

In one embodiment, $R^3$ may be substituted with one or more functional groups selected from the group of a halogen, a carboxylic acid, a carboxylic acid ester, and a carboxylic acid anhydride. Further the cyclic carboxylic anhydride may be selected from the group of succinic anhydride, maleic anhydride, itaconic anhydride, aconitic anhydride, phthalic anhydride, pyromellitic dianhydride, and 1,2,4,5-cycloheanetetracarboxylic dianhydride.

In the method, of this embodiment, the cyclic carboxylic anhydride may be unsaturated such that the functionalized fluorinated monomer made thereby has a carbon-carbon double bond. In such an embodiment, the unsaturated functionalized fluorinated monomer may be polymerized via free radical polymerization to form a fluorinated polyacrylate or a fluorinated polystyrene or co-polymers and blends thereof. Further, the unsaturated functionalized fluorinated monomer from this embodiment is reactive and can be used in addition reactions, such as the Michael Addition reaction mechanism to form chain-extended functionalized fluorinated monomers.

In the embodiment herein wherein a functionalized fluorinated monomer is made by reacting at least one fluorinated alcohol with a cyclic carboxylic anhydride such that the functionalized fluorinated monomer has a carboxylic acid group and an ester linkage, the invention further includes a method for making a polymer comprising polymerizing the functionalized fluorinated monomer to form a fluorinated polyester via condensation polymerization. Also within the scope of this embodiment are functionalized fluorinated monomers made from the method of reacting at least one fluorinated alcohol with a cyclic carboxylic anhydride. Further included are compositions for making functionalized fluorinated monomers having a carboxylic acid group and an ester linkage, comprising a fluorinated alcohol and a cyclic carboxylic acid anhydride.

The present invention further includes a method for making chain-extended fluorinated monomers or oligomers comprising reacting one or more functionalized fluorinated monomer(s) made by any of the methods recited herein with one or more cyclic reactant(s). The cyclic reactant(s) is/are preferably selected from one or more of cyclic carboxylic acid anhydride, cyclic ether, cyclic carbonate, and a cyclic ester, Preferred cyclic ethers include propylene oxide, glycidol, epichlorohydrin, butyl gylcidyl ether, and 2-ethyhexyl glycidyl ether. Preferred cyclic esters include L-lactide, D,L-lactide, glycolide and ε-caprolactone, with ε-caprolactone being most preferred. Preferred cyclic carbonates include ethylene carbonate, propylene carbonate and trimethylene carbonate, with trimethylene carbonate being most preferred. Preferred carboxylic acid anhydrides include succinic anhydride, maleic anhydride, itaconic anhydride, aconitic anhydride, phthalic anhydride, hexahydrophthalic anhydride, trimellitic anhydride, and 1,2,4-cyclohexanetricarboxylic anhydride.

In a preferred embodiment of such a method for making chain-extended fluorinated monomers or oligomers, the functionalized fluorinated monomer may be a fluorinated diol having at least one ether linkage and the chain-extended fluorinated monomer may be a fluorinated dicarboxylic acid. The invention also includes the chain-extended fluorinated monomers formed by this embodiment of the method herein. Further included in such an embodiment is a method for making a polymer or oligomer, comprising polymerizing the chain extended functionalized fluorinated monomer having at least one carboxylic acid group as via condensation polymerization to form a fluorinated polyester.

The present invention further includes chain-extended functionalized fluorinated monomers made by reacting one or more functionalized fluorinated monomer(s) made by one of the methods recited herein with one or more cyclic reactant(s).

Further, the present invention includes a method for making a polymer, comprising reacting a first reactant having at least one hydroxyl group with a cyclic ester, a cyclic carbonate, or a cyclic ether via ring opening polymerization to form a fluorine-containing polyester polyol ester, a fluorine-containing polycarbonate polyol or a fluorine-containing polyether polyol, respectively, wherein the first reactant having the at least one hydroxyl group is selected from (i) a functionalized fluorinated monomer having at least one hydroxyl group formed by the method of reacting at least one fluorinated nucleophilic reactant having a functional reactant group with at least one compound comprising at least one epoxide group; or (ii) a chain extended fluorinated monomer or a chain extended fluorinated oligomer, which is formed by reacting (a) a functionalized fluorinated monomer having at least one hydroxyl group formed by the method of reacting at least one fluorinated nucleophilic reactant having a functional reactant group with at least one compound comprising at least one epoxide group with (b) a cyclic reactant selected from a group of a cyclic carbonate, a cyclic ether, and a cyclic ester.

The present invention also relates to polymers or oligomers made by polymerizing any of the hydroxy-, carboxylic acid ester- or carboxylic acid-functionalized fluorinated monomers or chain extended functionalized fluorinated monomers made by any of the methods recited herein, to form fluorinated polyesters via condensation polymerization.

The present invention further relates to polymers or oligomers made by polymerizing any of the hydroxyl functionalized fluorinated monomers or chain extended functionalized fluorinated monomers made by any of the methods recited herein, to form fluorinated polycarbonates via condensation polymerization.

In another embodiment of the present invention, the present invention includes a method for making a polyamino-functionalized fluorinated monomer comprising reacting an unsaturated fluorinated monomer with at least one polyamine to form a polyamino-functionalized fluorinated monomer. The unsaturated fluorinated monomer may comprise an ester linkage. Further, the unsaturated fluorinated monomer may be a fluorinated maleate or selected from 2,2,2-trifluoroethyl methacrylate, and 3,3,4,4,5,5,6,6,7,7,8,8,8-tridecafluoro-1-octyl methacrylate, among others. The polyamine in this embodiment may be at least one of 1,6-diaminohexane; 2-methyl-1,5-diaminopentane; 4,4'-diaminodicyclohexylmethane; and 3,3-dimethyl-4,4'-diaminodicyclohexyl methane.

The present invention also includes a polyamino-functionalized fluorinated monomer made by reacting an unsaturated fluorinated monomer with a polyamine. Also provided are compositions for making polyamino-functionalized fluorinated monomers, comprising an unsaturated fluorinated monomer and a polyamine.

Further provided are methods for making a polymer comprising polymerizing a polyamino-functionalized fluorinated monomer made by the method embodiment described herein with a polyisocyanate via condensation polymerization to form a fluorinated polyurea.

Also included within the invention are methods for using functionalized fluorinated monomers made according to the disclosure herein that contain reactive functional groups to modify existing polymers or oligomers. The method includes modifying an existing polymer or oligomer by providing a functionalized fluorinated monomer having at least one reactive functional group; and reacting the at least one reactive functional group of the functionalized fluorinated monomer with either or both of a reactive end group on the polymer or oligomer or a reactive functional group on the backbone of the polymer or oligomer.

In one embodiment of the method of modifying a polymer or oligomer, the functional group of the functionalized fluorinated monomer is preferably a hydroxyl group and the reactive functional group of the polymer or oligomer is preferably a cyclic anhydride, and the polymer or oligomer is preferably selected from free radically polymerized copolymers of maleic anhydride with one or more of styrene, methyl methacrylate, butadiene and ethylene.

In another embodiment of the method, the functional group of the functionalized fluorinated monomer may be a carboxylic acid group and the reactive functional group of the polymer or the oligomer may be an epoxide group, and wherein the polymer or oligomer may be selected from copolymers of glycidyl acrylate and/or glycidyl methacrylate, epoxy resins, polymers and copolymers of bisphenol A diglycidyl ether.

In a further embodiment of the method, the functional group of the functionalized fluorinated monomer may be an amino group and the reactive functional group of the polymer or oligomer may be a cyclic anhydride group derived from maleic anhydride, an isocyanate or an epoxide, and the polymer or oligomer may be a free radically polymerized copolymer of maleic anhydride with one or more of styrene, methyl methacrylate, butadiene, and ethylene, a polyisocyanate, a copolymer of glycidyl acrylate or glycidyl methacrylate or a polymer or oligomer of bisphenol A diglycidyl ether.

In yet a further embodiment of the method, the functional group of the functionalized fluorinated monomer may be an epoxide group and the reactive functional group of the polymer or oligomer may be a carboxylic acid group, and the polymer or oligomer may be a homopolymer or copolymer of acrylic acid or methacrylic acid, a polyester, or a polyamide. Further, in one method of modifying a polymer or an oligomer according to this embodiment, the reaction occurs during an extrusion process, whereby a composition comprising the polymer or oligomer and the functionalized fluorinated monomer is fed into an extruder and the reaction occurs during heat melting.

The functional group of the functionalized fluorinated monomer in the method of modifying the polymer or oligomer may be a carboxylic anhydride group and the reactive functional group of the polymer or oligomer may be a hydroxyl or amino group, and the polymer or oligomer may be a polyvinyl alcohol, a polyester, or a polyamide. In such an embodiment, the reaction may occur during an extrusion process, whereby a composition comprising the polymer or oligomer and the functionalized fluorinated monomer is fed into an extruder and the reaction occurs during heat melting.

DETAILED DESCRIPTION OF THE INVENTION

The present invention provides methods for making functionalized fluorinated monomers useful in the formation of polymers and oligomers applied in polymer-based systems, such as coatings, to provide improved surface properties, such as graffiti-resistance, stain-resistance, self-cleaning ability, hydrophobicity, and transparency, among others. The functionalized fluorinated monomers allow for improvement in surface properties when incorporated into polymers at low concentrations and some embodiments provide improved surface properties at a significantly lower cost relative to conventional methods used to improve surface properties in polymer-based systems. Further, the fluorine-containing oligomers or polymers of the present invention can be used to produce articles with improved abrasion-resistance and other surface hardness related properties in comparison to conventional fluorinated polyether block-containing polymers. The fluorine-containing oligomers or polymers of the present invention can also be used to produce articles with greatly improved transparency in comparison to conventional fluorinated polyether block-containing polymers. The fluorinated oligomers or polymers produced by the methods described herein may also be used as additives in lubricating compositions for applications such as metal forming, metal working, and as additives in automotive lubricants, such as motor oils and gear oils.

As used herein, "made," "making" or "make" are intended to include something that is formed, produced, results from a reaction, or is otherwise created. As used herein, the term "poly" means more than one, for example, a "polyol" may include a "diol," An "oligomer" is a low molecular weight form of a repeating molecule wherein the repeating unit is present two or more times in the molecule. A "polymer" is intended to include larger molecules including repeating units and if not otherwise differentiated can be interpreted to encompass within its scope an oligomer.

In one embodiment, the present invention relates to a method for making a functionalized fluorinated monomer by reacting at least one fluorinated nucleophilic reactant having a reactive functional group with at least one compound having at least one epoxide group to form a functionalized fluorinated monomer having at least one hydroxyl group. The at least one fluorinated nucleophilic reactant is preferably selected from a fluorinated alcohol, a fluorinated carboxylic acid, a fluorinated organic acid anhydride, a fluorinated amine, a fluorinated amide, a fluorinated sulfonamide, and a fluorinated thiol.

The fluorinated nucleophilic reactant may be a mixture of two or more fluorinated nucleophilic reactants, such as a fluorinated alcohol and a fluorinated thiol. However, the reaction preferably involves a single fluorinated nucleophilic reactant, such as a fluorinated alcohol. In alternate embodiments, the fluorinated nucleophilic reactant may include two or more fluorinated nucleophilic reactants of the same type or of a different type, such as two fluorinated alcohols or a fluorinated alcohol and a fluorinated thiol. The molar ratio of the fluorinated nucleophilic reactant to the compound having at least one epoxide group is preferably about 0.3 to about 1.5, and is more preferably about 0.5 to about 1.1.

The compound having at least one epoxide group may have multiple epoxide groups and thus may be a di-epoxide, such as a diglycidyl ether. In embodiments having multiple epoxide groups, the functionalized fluorinated monomer made can have one hydroxyl group for each epoxide group in the epoxide-containing compound. As a result, the functionalized fluorinated monomer can be a diol or polyol.

Suitable epoxide-containing molecules include, but are not limited to ethylene oxide; propylene oxide; glycidol; 1,2-epoxycyclohexane; 2,3-epoxy-5-methylhexane; epichlorohydrin; butene oxide; styrene oxide; cyclopentene oxide; 1,3-butadiene diepoxide; butyl glycidyl ether; 2-ethylhexyl glycidyl ether; neodecanoic acid glycidyl ester; bisphenol A diglycidyl ether; ethylene glycol diglycidyl ether; 1,3-propanediol diglycidyl ether; 1,4-butanediol diglycidyl ether; neopentyl glycol diglycidyl ether; glycerol diglycidyl ether; resorcinol diglycidyl ether; hydroquinone diglycidyl ether; 1,4-cyclohexanedimethanol diglycidyl ether; 1,6-hexanediol diglycidyl ether; bis(3,4-epoxycyclohexylmethyl)adipate; 3,4-epoxycyclohexylmethyl-3,4-epoxycyclohexanecaThoxylate; trimethylolpropane triglycidyl ether; sorbitol polyglycidyl ether; and pentaerythritol tetraglycidyl ether. Preferably, the compound comprising at least one epoxide group is selected from 1,4-butanediol diglycidyl ether; 1,4-cyclohexanedimethanol diglycidyl ether; 1,6-hexanediol diglycidyl ether; 3,4-epoxycyclohexylmethyl-3,4-epoxycyclohexanecarboxylate; bis(3,4-epoxy-cyclohexylmethyl)adipate; trimethylolpropane triglycidyl ether; sorbitol polyglycidyl ether; and pentaerythritol tetraglycidyl ether.

When the at least one fluorinated nucleophilic reactant is a fluorinated alcohol, the resulting functionalized fluorinated monomer has an ether linkage. Any of various fluorinated alcohols may be used, including but not limited to: 2,2,2,-trifluoroethanol; 2,2,3,3,3-pentafluoro-1-propanol; 1,4,4-heptafluoro-1-butanol; 2,2,3,3,4,4,5,5,5-nonafluoro-1-pentanol; 2,2,3,3,4,4,5,5,6,6,7,7,8,8,8-pentadecafluoro-1-octanol; 1,1,1,3,3,3-hexafluoro-2-propanol; 1,1,1-trifluoro-2-butanol 2,2,3,3-tetrafluoro-1-propanol; 3,5-bis(trifluoromethyl)benzyl alcohol; 2,3,4,5,6-pentafluorobenzyl alcohol; 3-hydroxyphenylsulfur pentafluoride; 4-hydroxyphenylsulfur pentafluoride; tetrafluoroethylene-based telomer alcohols including 3,3,4,4,5,5,6,6,7,7,8,8,8-tridecafluoro-1-octanol and fluorinated ether-based alcohols, such as 2-perfluoropropoxy-2,3,3,3-tetrafluoropropanol. In a preferred embodiment, the fluorinated alcohol is selected from the group of 2,2,2,-trifluoroethanol; 2,2,3,3,3-pentafluoro-1-propanol; 1,1,1,3,3,3-hexafluoro-2-propanol; 4-hydroxyphenylsulfur pentafluoride; 2-perfluoropropoxy-2,3,3,3-tetrafluoropropanol, and 3,3,4,4,5,5,6,6,7,7,8,8-tridecafluoro-1-octanol.

The reaction of the fluorinated alcohol and the compound having at least one epoxide group may take place in the presence of a base catalyst, wherein the fluorinated monomer made by the reaction will contain the corresponding number of ether linkages and secondary hydroxyl groups. In such embodiments, the fluorinated monomer preferably has a structure according to formula (I):

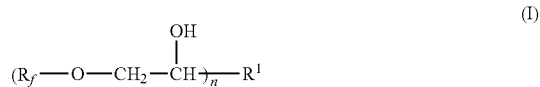

(I)

The $R_f$ group can be a partially or fully fluorinated, branched or unbranched, substituted or unsubstituted alkyl group having one to about eighteen carbon atoms. When the $R_f$ group is an alkyl group, the $R_f$ group may further having 0 to about 6 ether linkages. When the $R_f$ group is an alkyl group and is substituted, the $R_f$ group may include an aromatic group, a sulfur pentafluoride group, a halogen atom, or a combination thereof. The $R_f$ group can alternately be a partially or fully fluorinated, substituted or unsubstituted aryl group. When $R_f$ is an aryl group and is substituted, $R_f$ may include a sulfur pentafluoride group, a halogen atom, or a combination thereof. The $R^1$ group is derived from the epoxide-containing molecule and can be hydrogen, $R_f$, or a saturated or unsaturated, branched or unbranched, substituted or unsubstituted alkyl group, cyclic alkyl group, or heterocyclic group. The $R^1$ group preferably has 1 to about 24 carbon atoms. When $R^1$ is an alkyl group, a cyclic alkyl group, or a heterocyclic group, $R^1$ may further include 0 to 6 ether linkages, ester linkages, or aryl groups. Further, the $R^1$ group, when substituted, includes a functional group selected from the group of a hydroxyl group, a halogen, an epoxide, a carboxylic acid, a carboxylic acid ester, a carboxylate salt, an amine, a thiol, and combinations thereof. Further, n is preferably 1 to about 4.

When $R_f$ is an unbranched alkyl group, $R_f$ preferably has a structure according to the foil owing formula:

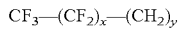

wherein x is from 0 to about 10, and y is from 1 to about 10. More preferably, x is from 0 to about 5, and y is preferably from 0 to about 10.

Preferred structures for $R_f$ when $R_f$ is an unbranched alkyl group include:

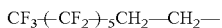

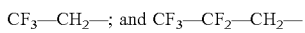

Other preferred structures for $R_f$ include:

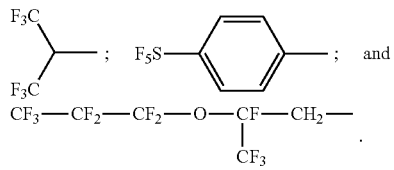

Further, in formula (I), $R^1$ may be derived from a diglycidyl ether having a structure according to the general formula:

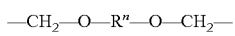

wherein $R^n$ is preferably a saturated, branched or unbranched, alkyl group having one to about ten carbon atoms and may include one or more cyclic groups, ether linkages, or ester linkages.

Other preferred structures for $R^1$ are selected from the group of:

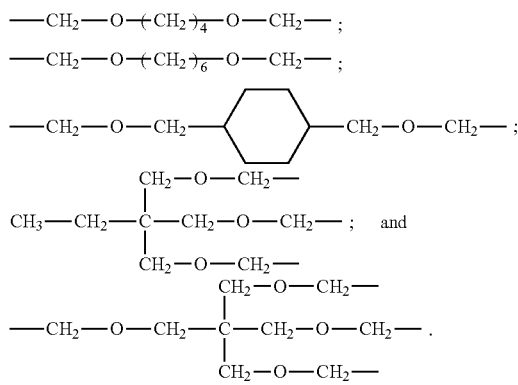

Suitable base catalysts useful for producing the functionalized fluorinated monomer of formula (I) include, but are not limited to: alkali metal hydroxides, hydrides and alkoxides, such as lithium hydroxide, sodium hydroxide, sodium hydride, sodium methoxide and potassium hydroxide; alkaline earth metal hydroxides, such as magnesium hydroxide and calcium hydroxide; alkali and alkaline earth metals, such as sodium and potassium; quaternary ammonium hydroxides, such as tetramethyl ammonium hydroxide and tetrabutylammonium hydroxide; and tertiary amines, such as trimethylamine, triethylamine, triisopropylamine, and DBU.

Alternately, the reaction of the fluorinated alcohol and the compound having at least one epoxide group may take place in the presence of an acid catalyst, wherein the functionalized fluorinated monomer made by the reaction contains an ether linkage and a primary hydroxyl group or groups. In such embodiments, the fluorinated monomer preferably has a structure according to formula (II):

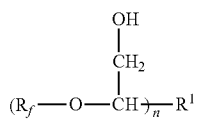

In the acid catalyzed reaction, the $R_f$, $R^1$ and n are the same as defined above with respect to the base catalyzed reaction of a fluorinated alcohol and a compound having at least one epoxide group. Preferred $R_f$ and $R^1$ groups are the same as set forth above with respect, to formula (I), Suitable acid catalysts include, but are not limited to hydrochloric acid, sulfuric acid and methanesulfonic acid.

When the reaction involves a fluorinated nucleophilic reactant that is a fluorinated carboxylic acid reacted with a compound having at least one epoxide group, the functionalized fluorinated monomer has at least one hydroxyl group and an ester linkage. The fluorinated monomer preferably has a structure according to formula (III):

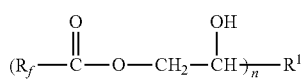

In such embodiments, the $R_f$ group of the functionalized fluorinated monomer is derived from the fluorinated carboxylic acid and is connected via an ester linkage derived from the carboxylic acid. Further, the epoxide ring of the epoxide-containing compound opens to form a hydroxyl group. In this embodiment, $R_f$, $R^1$ and n are the same as defined above with respect to formulas (I) and (II).

In formula (III), when $R_f$ is an unbranched alkyl group, $R_f$ preferably has a structure according to the following formula:

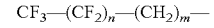

wherein n is 0 to about 10 and m is 0 to about 10. Preferred structures for $R_f$ when $R_f$ is an unbranched alkyl group include the following structures:

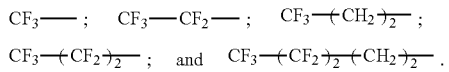

In formula (III), other preferred structures for $R_f$ include the following:

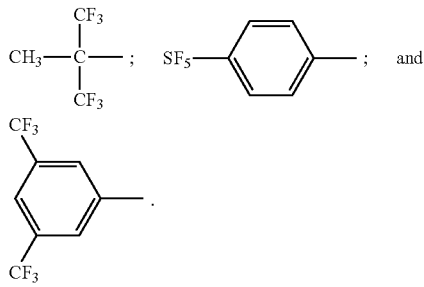

In formula (III), preferred structures for $R^1$ are the same as those set forth with respect to formula (I).

Suitable fluorinated carboxylic acids include, but are not limited to trifluoroacetic acid; pentafluoropropionic acid; 2,2-bis(trifluoromethyl)propionic acid; 4,4,4-trifluorobutyric acid; heptafluorobutyric acid; 4,4,5,5,6,6,6-heptafluorohexanoic acid; perfluorohexanoic acid; perfluoroheptanoic acid; nonafluoro-3,6-dioxaheptanoic acid; perfluoro-3,6-dioxadecanoic acid; 2,3,4,5,6-pentafluorobenzoic acid; trifluoromethylbenzoic acid; trifluoromethoxybenzoic acid; 3,5-bis(trifluoromethyl)benzoic acid; 3,5-bis(trifluoromethyl)phenylacetic acid; 3-pentafluorothiobenzoic acid; 4-pentafluorothiobenzoic acid; 4,8-dioxa-3H-perfluorononanoic acid; perfluoro(2-ethyloxy-ethoxy)acetic acid; and perfluoro(2-methyl-3-oxa)hexanoic acid. In a preferred embodiment, the fluorinated carboxylic acid is selected from the group of trifluoroacetic acid; pentafluoropropionic acid; 2,2-bis(trifluoromethyl)propionic acid; 4,4,4-trifluorobutyric acid; heptafluorobutyric acid; 4,4,5,5,6,6,6-heptafluorohexanoic acid; 4-pentafluorothiobenzoic acid; and 3,5 bis(trifluoromethyl)benzoic acid.

When the fluorinated nucleophilic reactant is a fluorinated amine, the functionalized fluorinated monomer has at least one hydroxyl group and an amine group. Preferably, the functionalized fluorinated monomer has a structure according to formula (IV):

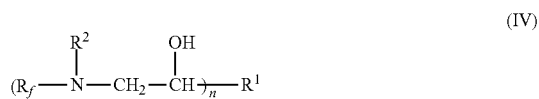

(IV)

The $R_f$ group is the same as described above with reference to formula (I)-(III), and the $R_f$ group is derived from the fluorinated amine as is the amine group. The hydroxyl group is made by the ring opening of the epoxide-containing compound, and the $R^1$ group is also derived from the epoxide-containing compound. Thus, $R^1$ and n are also the same as described above. $R^2$ can be a hydrogen atom or an $R_f$ group. Alternately, $R^2$ can be a saturated, branched or unbranched, alkyl group of one to about six carbon atoms, and may be substituted or unsubstituted. When $R^2$ is substituted, $R^2$ may have one or more functional groups selected from the group of a hydroxyl group, a halogen, an epoxide, a carboxylic acid, a carboxylic acid ester, a carboxylate salt, an amine, a thiol, and combinations thereof.

In formula (IV), $R_f$ preferably has a structure selected from the group of

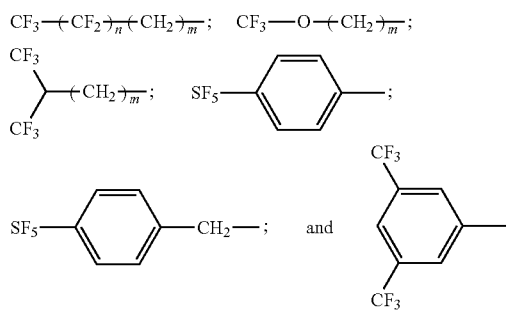

wherein n is 0 to about 10 and m is 0 to about 10.

In formula (IV), preferred structures for $R^1$ are the same as those set forth with respect to formula (I). $R^2$ preferably has a structure selected from the group of $R_f$, hydrogen, and $CH_3-(CH_2)_m-$; wherein in is 1 to about 10.

Any of various fluorinated amines may be used, including but not limited to: 2,2,2-trifluoroethylamine; 3,3,3-trifluoropropylamine; 4,4,4-trifluorobutylamine; 7,7,7-trifluoroheptanamine; 1H,1H-perfluoropentylamine; 1H,1H-perfluorohexylamine; 1H,1H,2H,2H-perfluoroheptylamine; 1H,1H-perfluoroheptylamine; 1H,1H,2H,2H-perfluorooctylamine; 4,4,4-trifluoro-3-(trifluoromethyl)butan-1-amine; bis(2,2,2-trifluoroethyl)amine; bis(3,3,3-trifluoropropyl)amine; 2-(trifluoromethoxy)ethan-1-amine; 3-(trifluoromethoxy)propan-1-amine; 4-(trifluoromethoxy)butan-1-amine; bis[2-(trifluoromethoxy)ethyl]amine; bis(4,4,4-trifluorobutyl)amine; 3,3,3-trifluoro-2,2-dimethylpropan-1-amine; 3,5-bis(trifluoromethyp)benzylamine; 3,3,3-trifluoropropane-1,2-diamine; 3-aminophenylsulfur pentafluoride; 4-aminophenylsulfur pentafluoride; 4-(pentafluorosulfur)benzylamine; 3,4-diaminophenylsulfur pentafluoride; and 3,5-diaminophenylsulfur pentafluoride.

When the fluorinated nucleophilic reactant is a fluorinated amide, the functionalized fluorinated monomer has at least one hydroxyl group and an amide linkage. Preferably, the reaction takes place in the presence of a base catalyst. The functionalized fluorinated monomer made by the reaction of the fluorinated amide and the compound having at least one epoxide group preferably has a structure according to formula (V):

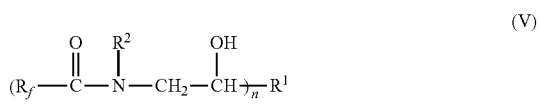

(V)

The $R_f$ group and the amide linkage are derived from the fluorinated amide, while the hydroxyl group is made by the ring opening of the epoxide group. The $R_f$, $R^1$, $R^2$ groups and n are the same as described above with respect to formula (IV). Further, the preferred structures for $R_f$, $R^1$ and $R^2$ are also the same as set forth above with respect to formula (IV).

Any of various fluorinated amides may be used, including but not limited to 2,2,2-trifluoroacetamide, pentafluoropropanamide, 4,4,4-trifluorobutanamide, perfluorobutanamide, perfluoropentanamide, perfluorohexanamide, perfluoroheptanamide, 2,2-bis(trifluoromethyl)propanamide, 4,4,5,5,6,6,6-heptafluorohexanamide, 3,5-bis(trifluoromethyl)phenylacetamide, 3-pentafluorothiobenzamide, pentafluorothiobenzamide, perfluoro(2-ethyloxy-ethoxy)acetamide, perfluoro(2-methyl-3-oxahexan)amide; and 3,5-bis(trifluoromethyl)benzamide. Preferably, the fluorinated amide is 2,2,2-trifluoroacetamide.

When the fluorinated nucleophilic reactant is a fluorinated sulfonamide, the functionalized fluorinated monomer has at least one hydroxyl group and a sulfonamide linkage. Preferably, the reaction takes place in the presence of a base catalyst. The functionalized fluorinated monomer made by the reaction of a fluorinated sulfonamide and a compound having at least one epoxide group preferably has a structure according to formula (VI):

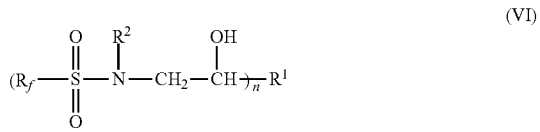

(VI)

The $R_f$ group and sulfonamide linkage is provided by the fluorinated sulfonamide, and the hydroxyl group and $R^1$ group are derived from the epoxide. The $R_f$ group, $R^1$, $R^2$ and iv are the same as described above for formula (IV). Further, the preferred structures for $R_f$, $R^1$ and $R^2$ are also the same as set forth above with respect to formula (IV).

Any of various fluorinated sulfonamides may be used, including but not limited to trifluoromethanesulfonamide; 2,2,2-trifluoroethanesulfonamide; pentafluoroethylsulfonamide; 3,3,3-trifluoropropane-1-sulfonamide; perfluorobutylsulfonamide; perfluorohexanesulfonamide; pentafluorobenzenesulfonamide; and 3,5-bis(trifluoromethyl)benzene sulfonamide. Preferably, the fluorinated sulfonamide is selected from the group of trifluoromethanesulfonamide; 2,2,2-trifluoroethanesulfonamide; and perfluorobutylsulfonamide.

When the fluorinated nucleophilic reactant is a fluorinated thiol, the resulting functionalized fluorinated monomer will contain the corresponding number of thioether linkages and hydroxyl groups. The reaction of the fluorinated thiol and the compound having at least one epoxide group may take place in the presence of a base catalyst. Suitable base catalysts include, but are not limited to: alkali metal hydroxides, such as lithium hydroxide, sodium hydroxide and potassium hydroxide; alkaline earth metal hydroxides, such as magnesium hydroxide and calcium hydroxide; quaternary ammonium hydroxides, such as tetramethylanrrrronium hydroxide and tetrabutylammonium hydroxide; and tertiary amines, such as trimethylamine, triethylamine, triisopropylamine, and DBU. Preferably, the fluorinated monomer made by the reaction of a fluorinated thiol and a compound having at least one epoxide group that has a structure according to formula (VII):

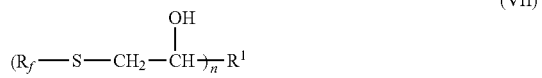

(VII)

The $R_f$ group and the thioether linkage are derived from the fluorinated thiol. The hydroxyl group is made by the ring opening of the epoxide group and the $R^1$ group is also derived from the epoxide-containing compound. The $R_f$ group, $R^1$ group, and n are the same as described above for each formula, as for example for formula (I). The $R_f$ group preferably has a structure according to the following formula:

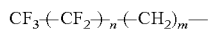

wherein n is 1 to about 10 and m is 1 to about 10. Further, preferred structures for $R^1$ are the same as those set forth above with respect to formula (I).

Any of various fluorinated thiols may be used, including but not limited to 2,2,2,-trifluoroethanethiol 3,3,3-trifluoropropanethiol; 2,2,3,3,3-pentafluoro-1-propanethiol; 2,2,3,3, 4,4,4-heptafluoro-1-butanethiol; 2,2,3,3,4,4,5,5,5-nonafluoro-1-pentanethiol; 2,2,3,3,4,4,5,5,6,6,7,7,8,8,8-pentadecafluoro-1-octanethiol; 1H, 1H,2H,2H-perfluorooctane-1-thiol; 1H,1H,2H,2H-perfluorodecane-1-thiol; 9,9,10,10,11,11,12,12,12-nonafluorododecane-1-thiol; 12,12,12-trifluorododecanethiol, 1H,1H,2H,2H-perfluorohexane-1-thiol; and 4,4,5,5,5-pentafluoropentane-1-thiol.

When the fluorinated nucleophilic reactant is a fluorinated organic acid anhydride, the functionalized fluorinated monomer has at least one hydroxyl group and an ester linkage. The functionalized fluorinated monomer preferably has a structure according to formula (III), which is the same structure as in the reaction of a fluorinated carboxylic acid and the compound comprising at least one epoxide group:

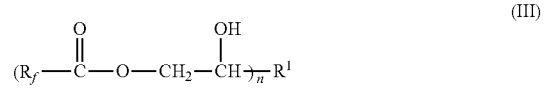

(III)

The $R_f$ group is derived from the carboxylic acid anhydride. The $R_f$ group, $R^1$ group and n are the same as discussed above with respect to the reaction of the fluorinated carboxylic acid and the compound comprising at least one epoxide group in formula (III), as discussed above. Preferred structures for $R_f$ and $R^1$ are also the same as those set forth above with respect to the reaction of the fluorinated carboxylic acid and the compound comprising at least one epoxide group.

Any of various fluorinated organic acid anhydrides may be used, including but not limited to trifluoroacetic anhydride; pentafluoropropionic anhydride; 2,2-bis(trifluoromethyl)propionic anhydride; 4,4,4-trifluorobutyric anhydride; heptafluorobutyric anhydride; 4,4,5,5,6,6,6-heptafluorohexanoic anhydride; perfluorohexanoic anhydride; perfluoroheptanoic anhydride; nonafluoro-3,6-dioxaheptanoic anhydride; perfluoro-3,6-dioxadecanoic anhydride; 2,3,4,5, 6-pentafluorobenzoic anhydride; trifluoromethylbenzoic anhydride; trifluoromethoxybenzoic anhydride; 3,5-bis(trifluoromethyl)benzoic anhydride; 3,5-bis(trifluoromethyl) phenylacetic anhydride; 3-pentafluorothiobenzoic anhydride; 4-pentafluorothiobenzoic anhydride; 4,8-dioxa-3H-perfluorononanoic anhydride; perfluoro(2-ethyloxy-ethoxy) acetic anhydride and perfluoro(2-methyl-3-oxa)hexanoic anhydride. In a preferred embodiment, the fluorinated organic acid anhydride is selected from the group of trifluoroacetic anhydride, pentafluoropropionic anhydride; 2,2-bis(trifluoromethyl)propionic anhydride; 4,4,4-trifluorobutyric anhydride; heptafluorobutyric anhydride; 4,4,5,5,6,6, 6-heptafluorohexanoic anhydride; 4-pentafluorothiobenzoic anhydride and 3,5 bis(trifluoromethyl)benzoic anhydride.

The present invention further relates to functionalized fluorinated monomers made by reacting at least one fluorinated nucleophilic reactant having a functional reactant group with at least one compound having at least one epoxide group. Preferably, the fluorinated nucleophilic reactant is selected from a fluorinated alcohol, a fluorinated carboxylic acid, a fluorinated organic acid anhydride, a fluorinated amine, a fluorinated amide, a fluorinated sulfonamide, and a fluorinated thiol. The resulting functionalized fluorinated monomers include at least one hydroxyl group, and further include a linkage depending upon the fluorinated nucleophilic reactant used (e.g. when the fluorinated nucleophilic reactant is a fluorinated alcohol, the resulting fluorinated monomer will have an ether linkage).

Functionalized fluorinated monomers derived from the fluorinated carboxylic acid, 3,5-bis(trifluoromethyl)benzoic acid ("BTFMBA") can be useful in the synthesis of fluorine-containing polyester polyols having improved transparency and hardness. In another embodiment, the fluorinated nucleophilic reactant may be a fluorinated alcohol, such as 2,2,2,-trifluoroethanol; 4-hydroxyphenyl sulfur pentafluoride and 3,3,4,4,5,5,6,6,7,7,8,8-tridecafluoro-1-octanol. Functionalized fluorinated monomers derived from these fluorinated alcohols can be useful in the synthesis of fluorine-containing polyester polyols having improved transparency and hardness. In a preferred embodiment, the fluorinated alcohol is 2,2,2-trifluoroethanol, which affords an economic advantage in the synthesis of the functionalized fluorinated monomers of the invention, due to the fact that it is available at a significantly lower cost than most fluorine-containing starting materials.

The present invention further relates to compositions for making functionalized fluorinated monomers including a fluorinated nucleophilic reactant having a functional reactant group and a compound having at least one epoxide group. Preferably, the fluorinated nucleophilic reactant is selected from a fluorinated alcohol, a fluorinated carboxylic acid, a fluorinated organic acid anhydride, a fluorinated amine, a fluorinated amide, a fluorinated sulfonamide, and a fluorinated thiol.

In another embodiment of the present invention, the present invention provides a method for making a functionalized fluorinated monomer by reacting at least one first reactant selected from a fluorinated mesylate, a fluorinated tosylate, and a fluorinated triflate, with at least one second reactant selected from an amine or polyamine; or an alcohol, polyol, phenol or polyphenol via an alkoxide intermediate or a phenoxyide intermediate, to form a functionalized fluorinated monomer.

The fluorinated mesylate, tosylate or triflate can be easily generated from the corresponding fluorinated alcohol by reacting it with methanesulfonyl chloride, p-toluenesulfonyl chloride or trifluoromethanesulfonyl chloride. A description of the synthesis and reactions of alkyl mesylates, tosylates and triflates is given in Solomons, T. W. Graham, Fryhle, C. B., "Organic Chemistry", 10$^{th}$ Edition, 2011, John Wiley & Sons, Inc., pages 518-521, which is incorporated herein in relevant part.

Suitable fluorinated alcohols for generating a fluorinated mesylate, tosylate, or triflate are the same as those discussed above with respect to the reaction of a fluorinated alcohol with an epoxide-containing compound.

When the second reactant is an amine, or polyamine, the functionalized fluorinated monomer resulting from the reaction is a fluorinated amine, Preferably, the reaction takes place according to formula (VIII):

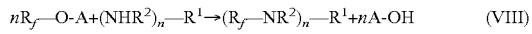 (VIII)

As noted above, the first reactant is preferably a fluorinated mesylate, a tosylate, or a triflate, and thus A may be selected from the group of:

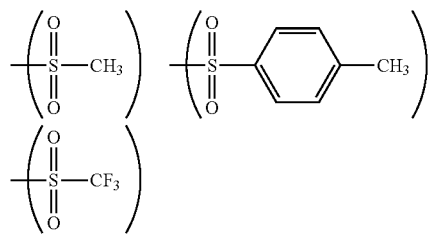

The $R_f$ group is a partially or fully fluorinated, branched or unbranched, substituted or unsubstituted alkyl group having one to about eighteen carbon atoms. When $R_f$ is an alkyl group, $R_f$ may include 0 to 6 ether linkages. When $R_f$ is an alkyl group and is substituted, $R_f$ may include an aromatic group, a sulfur pentafluoride group, a halogen atom, or a combination thereof. Alternately, $R_f$ may be a partially or fully fluorinated, substituted or unsubstituted aryl group. When $R_f$ is an aryl group and is substituted, $R_f$ may include a sulfur pentafluoride group, a halogen atom, or a combination thereof. $R^1$ can be a hydrogen atom or $R_f$. Further, $R^1$ may be a saturated or unsaturated, branched or unbranched, substituted or unsubstituted alkyl group, cyclic alkyl group or heterocyclic group having one to about twelve carbon atoms. When $R^1$ is an alkyl group, cyclic alkyl group or heterocyclic group, $R^1$ includes 0 to 6 ether linkages, ester linkages, or aryl groups. $R^2$ is hydrogen, $R_f$, or a saturated, branched or unbranched, substituted or unsubstituted alkyl group of one to about six carbon atoms. Additionally, n is preferably 1 to about 6. When $R^1$ and/or $R^2$ are substituted, $R^1$ and/or $R^2$ may have one or more functional groups selected from the group of a hydroxyl group, a halogen, a carboxylic acid, carboxylic acid ester, a carboxylate salt, an amine, a thiol, or a combination thereof. When $R^2$ is hydrogen, it may be possible to generate a di-substituted nitrogen with two attached $R_f$ groups.

Suitable amines and polyamines include, but are not limited to 1,2-diaminoethane, 1,2-diaminopropane, 1,3-diaminopropane, 1,4-diaminobutane, 1,5-diaminopentane, 1,6-diaminohexane, 2-methyl-1,5-diaminopentane, 2,5-diamino-2,5-dimethylhexane, 2,2,4-and/or 2,4,4-trimethyl-1,6-diaminohexane, 1,11-diaminoundecane 1,12-diaminododecane, 2-aminoethanol, diethanolamine, 3-amino-1,2-propanediol, 2-amino-2-methyl-1,3-propanediol, 2-amino-2-hydroxymethyl-1,3-propanediol, diethylenetriamine, triethylenetetramine, tetraethylenepentamine, 5-amino-1,3,3-trimethylcyclohexanemethylamine, 2,4 and/or 4,4'-diaminodicyclohexylmethane, 3,3'-dimethyl-4,4'-diaminodicyclohexylmethane, 3,3',5,5'-tetramethyl-4,4'-diaminodicyclohexylmethane, 2,2',3,3'-tetramethyl-4,4'-diaminodicyclohexylmethane, 2,4-and/or 2,6-hexahydrotoluene diamine, 2,4 and/or 2,6-diaminotoluene, 2,4' and/or 4,4'-diaminodiphenyl methane and polyether polyamines. In a preferred embodiment, the polyamine is selected from diethanolamine, diethylenetriamine, triethylenetetramine, tetraethylenepentamine, 1,6-diaminohexane, 2-methyl-1,5-diaminopentane, 4,4'-diaminodicyclohexylmethane, and 3,3'-dimethyl-4,4'-diaminodicyclohexylmethane.

In formula (VIII), $R_f$ preferably has a structure as set forth with respect to formula (I) above. Further, $R^1$ and $R^2$ preferably each have a structure that is selected from the group of:

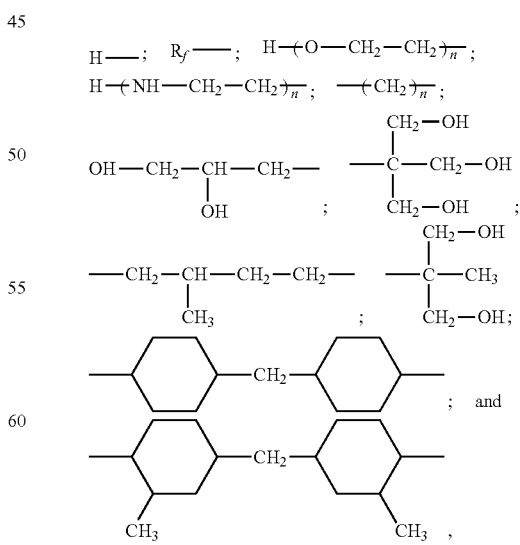

and n is 0 to about 10.

The reaction according to formula (Viii) takes place via nucleophilic substitution, wherein $R_f$ forms a bond with the nitrogen of the amine, and A-OH is produced as a byproduct. A non-nucleophilic base, such as potassium carbonate, triethylamine or diisopropylethylamine may be included to neutralize the A-OH byproduct. The molar ratio of fluorinated mesylate, tosylate or triflate to each equivalent of amine is preferably about 0.1 to about 1.5, and is more preferably about 0.5 to about 1. Preferably, the reaction takes place in a polar aprotic solvent, such as acetone, methyl ethyl ketone, acetonitrile, dimethyl formamide or dimethyl sulfoxide.

The reaction mixture is stirred at a temperature of about 25° C. to about 180° C. for about 3 to about 24 hours. The reaction ca n be carried out under an inert atmosphere to improve the color of the resulting product.

In embodiments of the reaction of a first reactant that is a fluorinated mesylate, a fluorinated tosylate, or a fluorinated triflate, wherein the second reactant is an alcohol, polyol, phenol, or polyphenol via an alkoxide intermediate or a phenoxide intermediate, the functionalized fluorinated monomer is a fluorinated ether. The alkoxide intermediate or phenoxide intermediate is generated from the corresponding alcohol by any of a number of methods, such as reacting it with a suitable base, as described in Streitwieser, A, Heathcock, C. H., "Introduction to Organic Chemistry", $2^{nd}$ Edition, 1981, Macmillen Publishing Co., Inc., pages 237-239, which is incorporated herein in relevant part.

Preferably, the functionalized fluorinated monomer is made by a reaction according to formula (IX):

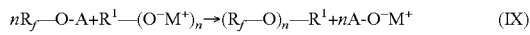

$nR_f\!-\!O\text{-}A+R^1\!-\!(O^-M^+)_n \rightarrow (R_f\!-\!O)_n\!-\!R^1+nA\text{-}O^-M^+$     (IX)

The $R_f$ group is the same as discussed above with respect to the reaction of a first reactant and a second reactant, wherein the second reactant is an amine. Further, $R^1$ and n are the same as discussed above with respect to formula (VIII) and $M^+$ is the counterion derived from the base used to generate the alkoxide or phenoxide intermediate.

Suitable alcohols, polyols, phenols and polyphenols include, but are not limited to ethylene glycol, propylene glycol, diethylene glycol, dipropylene glycol, triethylene glycol, glycerine, diglycerol, butylene glycol, 2-methyl-1,3-propanediol, 2,2-dimethyl-1,3-propanediol, 1,6-hexanediol, 2,2,4-trimethyl-1,3-pentanediol, trimethylolethane, trimethylolpropane, cyclohexanedimethanol, ditrimethylolpropane, pentaerythritol, dipentaerythritol, methyl 3,4,5-trihydroxybenzoate and dimethyl-5-hydroxyisophthalate.

Preferred structures for $R_f$ are the same as set forth above with respect to formula (I). In formula (IX), $R^1$ preferably has a structure selected from the following group:

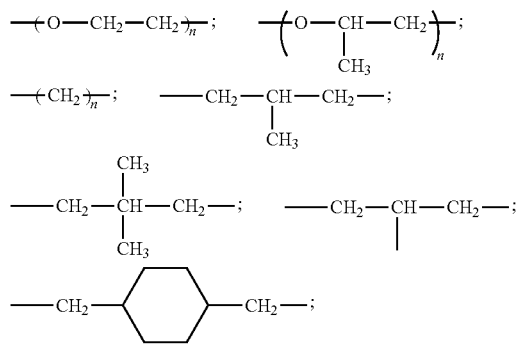

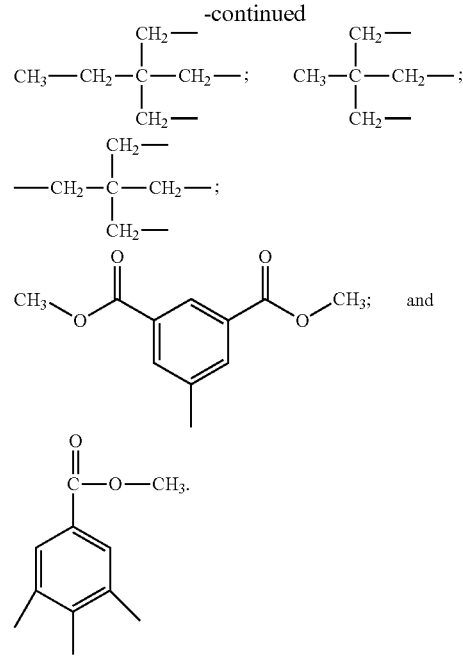

and n is 1 to about 6.

The reaction takes place via nucleophilic substitution wherein $R_f$ forms a bond with the alkoxide oxygen and $A\text{-}O^-M^+$ is produced as a byproduct. The molar ratio of fluorinated mesylate, tosylate or triflate to each equivalent of hydroxyl is preferably about 0.1 to about 1, and more preferably about 0.5 to about 1. Preferably, the reaction takes place in bulk, when reaction mixture is a liquid at reaction temperature, although polar aprotic solvents, such as acetone, methyl ethyl ketone, acetonitrile, dimethyl formamide and dimethyl sulfoxide, may be used, if necessary, wherein the reaction mixture is stirred at a temperature of about 25° C. to about 100° C. for about 3 to about 20 hours. The reaction can be carried out under an inert atmosphere to improve the color of the resulting product.

The present invention further provides functionalized fluorinated monomers made by the method of reacting a first reactant selected from a fluorinated mesylate, a fluorinated tosylate, and a fluorinated triflate, with a second reactant selected from an amine or polyamine, or an alcohol, polyol, phenol or polyphenol via an alkoxide intermediate or phenoxide intermediate. Further provided are compositions for making a functionalized fluorinated monomer, including a first reactant selected from a fluorinated mesylate, a fluorinated tosylate, and a fluorinated triflate, and a second reactant selected from an amine or polyamine; an alcohol, polyol, phenol or polyphenol, a alkoxide intermediate or a phenoxide intermediate.

In another embodiment of the present invention, the present invention provides a method for making a functionalized fluorinated monomer by reacting a fluorinated alkyl or aryl halide with an amine or a polyamine to form an amino-functionalized fluorinated monomer. The fluorinated alkyl or aryl halide is preferably a fluorinated iodide, although other fluorinated halogens, such as fluorinated bromides, may be used.

In a preferred embodiment, the fluorinated iodide is selected from 4-iodo-1,1,1-trifluorobutane, 6-iodo-1,1,1,2,2-pentafluorohexane, 3-(perfluorobutyl)propyl iodide, 1,1,1,2,2,3,3-heptafluoro-7-iodoheptane, and 1H, 1H,2H,2H-heptafluoro-3,3-bis(trifluoromethyl)-1-iodohexane. Further, the amine is preferably a primary or secondary amine.

Suitable amines and polyamines are the same as those discussed above with respect to the reaction of a fluorinated mesylate, tosylate or triflate with an amine, or polyamine.

Preferably, the functionalized fluorinated monomer is made by the representative reaction of formula (X):

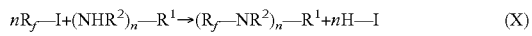  (X)

The $R_f$ group and $R^1$ group are the same as described above with respect to formulas (VIII) and (IX), and $R^2$ and n are the same as set forth with respect to formula (VIII). The reaction takes place via nucleophilic substitution, wherein the iodine is a leaving group and a bond is made between the carbon chain of the fluorinated halide and the nitrogen of the amine, and a hydrogen halide (e.g. H—I) is made as a byproduct. The molar ratio of fluorinated halide to each equivalent of amine is preferably about 0.1 to about 1, and more preferably about 0.5 to about 1.

In formula (X), $R_f$ preferably has a structure according to one of the following:

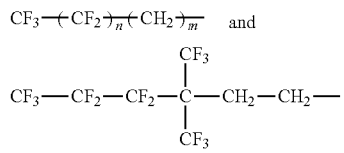

wherein n is 0 to about 10 and m is 0 to about 10. Preferred structures for $R^1$ and $R^2$ are the same as those set forth with respect to formula (VIII).

Further provided are functionalized fluorinated monomers made by reacting a fluorinated alkyl halide with either an amine or a polyamine. Also provided are compositions for making functionalized fluorinated monomers including a fluorinated alkyl halide and either an amine or a polyamine.

In another embodiment according to the present invention, the present invention provides a method for making a functionalized fluorinated monomer by reacting a fluorinated alcohol with an or aryl halide molecule having at least one functional group in the presence of a base catalyst to form a functionalized fluorinated monomer having an ether linkage and the at least one functional group derived from the alkyl or aryl halide molecule. In the case of alkyl halides, the reaction takes place via SN2 type nucleophilic substitution. In SN2 type nucleophilic substitution, one bond is made between a nucleophile and a carbon center of the substrate, while a bond between a leaving group and the carbon center of the substrate is broken. Thus, two reactants are involved in the rate determining step. In the case of aryl halides, the reaction takes place via aromatic nucleophilic substitution. The feasibility of aromatic nucleophilic substitution reactions is greatly enhanced by the presence of electron withdrawing groups on the aromatic ring of the aryl halide, such as nitro, cyano, and trifluoromethyl groups.

The fluorinated alcohol is preferably a primary or secondary alcohol. The alkyl or aryl halide molecule is preferably a primary or secondary alkyl halide. In one embodiment, the at least one functional group of the alkyl halide molecule is selected from the group of a hydroxyl group, an epoxide, a carboxylic acid, a carboxylic acid ester, a carboxylate salt, an amine, a thiol, and combinations thereof. Suitable alkyl or aryl halides include, but are not limited to 3-chloro-1,2-propanediol, 2,2-bis(bromomethyl)-1,3-propanediol, epichlorohydrin, 2,3-dichlorosuccinic acid, 4,5-dichloro-1,2-cyclohexanedicarboxylic acid, 2,3-dibromo-1-propanol, and 5-bromo-2-chlorobenzoic acid. The base catalyst is preferably an alkoxide, a hydride, or hydroxide of an alkali or alkaline earth metal. A thorough discussion of nucleophilic substitution reactions is given in Solomons, T. W. Graham, Fryhle, C. B., "Organic Chemistry," 10th Edition, 1984, John Wiley & Sons, Inc., pages 230-267, which is incorporated herein in relevant part.

In a preferred embodiment of this method, the reaction takes place by the following reaction formula (XI):

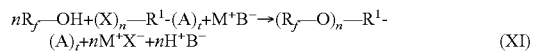  (XI)

In formula (XI), X is a halogen atom. $R_f$ is a partially or fully fluorinated, branched or unbranched, substituted or unsubstituted alkyl group having one to about eighteen carbon atoms. When $R_f$ is an alkyl group, $R_f$ may further have 0 to about 6 ether linkages. When $R_f$ is an alkyl group and is substituted, $R_f$ may include an aromatic group, a sulfur pentafluoride group, a halogen, or a combination thereof. Alternately, $R_f$ may be a partially or fully fluorinated, substituted or unsubstituted aryl group. When $R_f$ is an aryl group and is substituted, $R_f$ may include a sulfur pentafluoride group, a halogen atom, or a combination thereof. A is a functional group selected from a halogen, hydroxyl, epoxide, carboxylic acid, carboxylate salt, amine, and thiol. $R^1$ is a saturated, branched or unbranched, substituted or unsubstituted alkyl group, cyclic alkyl group, or heterocyclic group having one to about twelve carbon atoms, and when $R^1$ is an alkyl group, a cyclic alkyl group, or a heterocyclic group includes 0 to 6 ether linkages, ester linkages, or aryl groups. Further, $M^+$ is a metal or other cation, $B^-$ is a base; is preferably 1 to 4, and n is preferably 1 to about 6.

In formula (XI), $R_f$ preferably has a structure as set forth with respect to formula (I). Further, $R^1$ preferably has a structure selected from the following group:

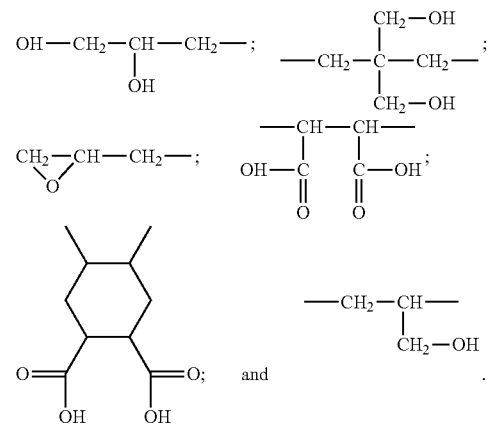

The reaction takes place in the presence of a base, B, such as hydroxide, alkoxide or hydride ion. The base deprotonates the hydroxyl group of the fluorinated alcohol to generate the corresponding alkoxide intermediate. The alkoxide oxygen forms a bond with the carbon center of the alkyl or aryl halide, and the halogen, X, serves as a leaving group. The halogen and the cation from the base form a halide salt byproduct, which is typically removed as a solid. The molar ratio of the fluorinated alcohol reactant to the each equivalent of halogen, X, is preferably about 0.3 to about 1.5, and more preferably about 0.5 to about 1.1. The reaction yields a functionalized fluorinated monomer containing an ether linkage and having an additional functionality A, from the alkyl halide.

The present invention further provides a functionalized fluorinated monomer made by the method of reacting at least one fluorinated alcohol with an alkyl or aryl halide molecule having at least one functional group in the presence of a base catalyst. Further provided is a composition for making a functionalized, fluorinated monomer including a fluorinated alcohol and an alkyl or aryl halide molecule having at least one functional group.

In another embodiment according to the present invention, the present invention relates to a method for making functionalized fluorinated monomers by reacting a fluorinated alcohol with a cyclic carboxylic acid anhydride to form a functionalized fluorinated monomer having a carboxylic acid group and an ester linkage. The molar ratio of the fluorinated alcohol to the each equivalent of anhydride is preferably about 0.3 to about 1.5, and more preferably about 0.5 to about 1.1. The reaction preferably takes place at a temperature of at least 80° C. The reaction may produce a functionalized fluorinated monomer according to formula (XII):

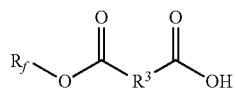

(XII)

The fluorinated alcohol breaks the cyclic carboxylic acid ring to form an ester linkage and a carboxylic acid group. The fluorinated alcohol can be any of those alcohols described above with respect to the reaction of a fluorinated alcohol with an epoxide-containing compound. Thus, $R_f$ is the same as set forth above with respect to formula (I). In formula (XII), preferred structures for $R_f$ are the same as those set forth with respect to formula (I).

Further, $R^3$ is a saturated or unsaturated, branched or unbranched, substituted or unsubstituted alkyl group, cyclic group, aryl group, or heterocyclic group having two to about eighteen carbon atoms. When $R^3$ is substituted, $R^3$ includes a halogen, a carboxylic acid, a carboxylic acid anhydride, or a combination thereof. Preferred structures for $R^3$ include the following structures:

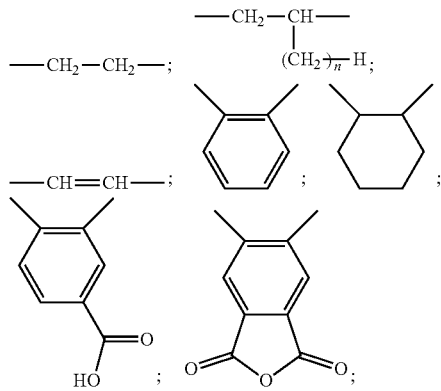

-continued

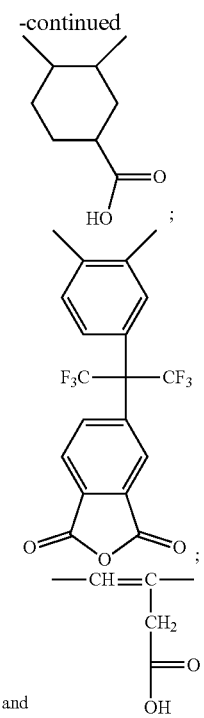

and n is 0 to about 10.

The cyclic carboxylic acid anhydride may also be a dianhydride, thereby resulting in a disubstituted dicarboxylic acid monomer containing two $R_f$ groups.

Suitable carboxylic acid anhydrides include, but are not limited to succinic anhydride; maleic anhydride; allyl succinic anhydride; butylsuccinic anhydride; dodecylsuccinic anhydride; octadecylsuccinic anhydride; phthalic anhydride; tetrahydrophthalic anhydride; hexahydrophthalic anhydride; 4-methylphthalic anhydride; trimellitic anhydride; 1,2,4-cyclohexanetricarboxylic anhydride; 1,2,3,4-cyclobutane tetracarboxylic dianhydride; pyromellitic dianhydride; 1,2,4,5-cyclohexanetetracarboxylic dianhydride; 4,4'-oxydiphthalic anhydride; 3,3',4,4'-benzophenone tetracarboxylic dianhydride; 3,3',4,4'-biphenyl tetracarboxylic anhydride; 2,2'-bis-(3,4-dicarboxyphenyl) hexafluoropropane dianhydride; itaconic anhydride; aconitic anhydride; 4-chlorophthalic anhydride; 4-bromophthalic anhydride; tetrachlorophthalic anhydride; tetrabromophthalic anhydride; citraconic anhydride; hexahydro-4-methylphthalic anhydride and chlorendic anhydride. In a preferred embodiment, the carboxylic acid anhydride is selected from succinic anhydride; maleic anhydride; itaconic anhydride; aconitic anhydride; phthalic anhydride; hexahydrophthalic anhydride; trimellitic anhydride; 1,2,4-cyclohexanetricarboxylic anhydride; pyromellitic dianhydride; and 1,2,4,5-cyclohexanetetracarboxylic dianhydride.

The cyclic carboxylic acid anhydride reacted with the fluorinated alcohol may be unsaturated such that the functionalized fluorinated monomer produced by the reaction contains a carbon-carbon double bond. The carbon-carbon double bond is capable of reaction via free radical copolymerization with ethylenically unsaturated monomers to produce fluorine-containing polymers. The present invention therefore provides a method for making a polymer by polymerizing an unsaturated fluorinated monomer, such as an unsaturated fluorinated monomer made by reaction of a fluorinated alcohol with an unsaturated cyclic carboxylic anhydride, via free radical polymerization to form a fluorinated polymer. A comprehensive description of the various methods used to synthesize polymers via free radical polymerization is given in Odian, G., "Principles of Polymerization," 4th Edition, 2004, John Wiley & Sons, Inc., pages 198-371, which is incorporated herein in relevant part.

The carbon-carbon double bond of the unsaturated fluorinated monomers of the invention is also able to undergo addition reactions, such as the Michael Addition, to chain-extend the functionalized fluorinated monomer. Michael Addition is a type of conjugate addition reaction that is used to form carbon-carbon bonds wherein a nucleophile is added to an $\alpha,\beta$-unsaturated carbonyl compound, i.e. a compound having an electron deficient carbon-carbon double bond. The Michael Addition is often base-catalyzed. It is often advantageous to convert the carboxylic acid group on the unsaturated fluorinated monomer to an ester by reacting it with an epoxide, such as butyl glycidyl ether, prior to carrying out the Michael Addition reaction.

The present invention additionally includes chain-extended monomers made by reacting the hydroxy-functional fluorinated monomers described above with cyclic reactants, such as cyclic carboxylic acid anhydrides, cyclic esters, cyclic carbonates, or cyclic ethers. The chain-extension reactions are potentially useful for improving the reactivity and/or other properties of the hydroxy-functional fluorinated monomers. In general, the chain-extension reactions increase the molecular weight of the functionalized fluorinated monomer, while allowing the location of the functional groups to be altered, or for the functional groups to be modified into alternate functional groups. In one example, chain-extension reactions can be used to convert secondary hydroxyl groups to more reactive primary hydroxyl groups or carboxylic acids. In another example, chain-extension reactions can be used to lower the volatility of a given hydroxy-functional fluorinated monomer, in order to afford its use at higher temperatures in subsequent reactions without significant losses. In a further example, chain extension reactions can be used to modify the physical properties of the hydroxy-functional fluorinated monomer, such as flexibility.

In one such embodiment, the present invention provides chain-extended functionalized fluorinated monomers made by reacting a hydroxy-functional fluorinated monomer with a cyclic carboxylic acid anhydride. Such chain-extended monomers have carboxylic acid functionality and ester linkages. Further provided are compositions for making chain-extended functionalized fluorinated monomers comprising a hydroxy-functional fluorinated monomer and a cyclic carboxylic anhydride.

Suitable carboxylic acid anhydrides include, but are not limited to succinic anhydride; maleic anhydride; allylsuccinic anhydride; butylsuccinic anhydride; dodecylsuccinic anhydride; octadecylsuccinic anhydride; phthalic anhydride; tetrahydrophthalic anhydride; hexahydrophthalic: anhydride; 4-methylphthalic anhydride; trimellitic anhydride; 1,2,4-cyclohexanetricarboxylic anhydride; itaconic anhydride; aconitic anhydride; 4-chlorophthalic anhydride; 4-bromophthalic anhydride; tetrachlorophthalic anhydride; tetrabromophthalic anhydride; citraconic anhydride; hexahydro-4-methylphthalic anhydride and chlorendic anhydride. In a preferred embodiment, the carboxylic acid anhydride is selected from succinic anhydride; maleic anhydride; itaconic anhydride; aconitic anhydride; phthalic anhydride; hexahydrophthalic anhydride; trimellitic anhydride and 1,2,4-cyclohexanetricarboxylic anhydride.

In another such embodiment, the present invention provides chain-extended functionalized fluorinated monomers made by reacting hydroxy-functional fluorinated monomers with cyclic esters. Such chain-extended monomers have hydroxyl functionality and ester linkages. Further provided are compositions for making chain extended functionalized fluorinated monomers comprising a hydroxy-functional fluorinated monomer and a cyclic ester.

The reaction may take place using any of various cyclic esters, including but not limited to: $\beta$-propiolactone, $\delta$-valerolactone, $\alpha$-methyl-$\delta$-valerolactone, $\epsilon$-caprolactone, $\alpha$-methyl-$\epsilon$-caprolactone, L-lactide, D,L-lactide, and glycolide. Preferably, the cyclic ester is $\epsilon$-caprolactone, L-lactide, D,L-lactide, or glycolide. Most preferably, the cyclic ester is $\epsilon$-caprolactone.

In another such embodiment, the present invention includes chain-extended functionalized fluorinated monomers made by reacting hydroxy-functional fluorinated monomers with cyclic carbonates. Such chain extended monomers have hydroxyl functionality and carbonate linkages. Further included are compositions for forming chain-extended functionalized fluorinated monomers comprising a hydroxyl-functional fluorinated monomer and a cyclic carbonate.

The reaction may take place using any of various cyclic carbonates, including but not limited to ethylene carbonate, propylene carbonate and trimethylene carbonate. Preferably the cyclic carbonate is trimethylene carbonate.

In another embodiment, the present invention includes chain-extended functionalized fluorinated monomers formed by reacting hydroxyl-functional fluorinated monomers with cyclic ethers. Such chain-extended monomers have hydroxyl functionality and ether linkages. Further provided are compositions for making chain-extended functionalized fluorinated monomers comprising a hydroxy-functional fluorinated monomer and a cyclic ether.

Any of various cyclic ethers may also be used, including but not limited to: ethylene oxide, propylene oxide, glycidol, 1,2-epoxycyclohexane, 2,3-epoxy-5-methylhexane, epichlorohydrin, butene oxide, styrene oxide, cyclopentene oxide, butyl glycidyl ether, 2-ethylhexyl glycidyl ether, trimethylene oxide, 3,3-dimethyloxetane and tetrahydrofuran. Preferably, the cyclic ether is selected from propylene oxide, glycidol, epichlorohydrin, butyl glycidyl ether, and 2-ethylhexyl ether.

Many combinations of fluorinated monomers and cyclic reactants are possible, and understandable to a person skilled in the art based on the disclosure, including the following reactions, which serve as representative examples for this class of reactions. In one example, the functionalized fluorinated monomer is a fluorine-containing diol and is reacted with two equivalents of a cyclic carboxylic acid anhydride to form the corresponding dicarboxylic acid as shown in the formula below:

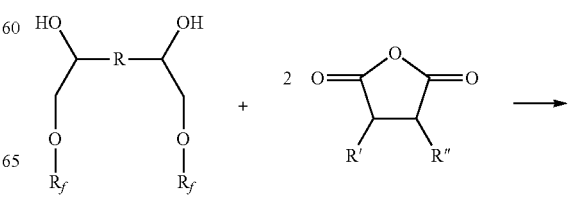

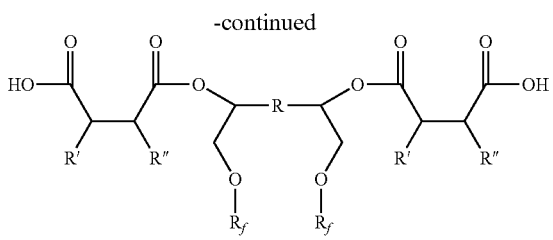

In this reaction, the fluorinated diol is reacted with a cyclic acid anhydride in a 1:2 molar ratio of the fluorinated diol to the cyclic acid anhydride, wherein Rr is a fluorinated alkyl or aryl group, and wherein R' and R" are hydrogen, alkyl groups, aryl groups, or are connected to each other to form a cycloaliphatic, aromatic, or heterocyclic ring. Each cyclic anhydride reacts with a hydroxyl group of the fluorinated diol via ring-opening to form an ester linkage, resulting in a chain-extended fluorinated monomer that is a fluorinated dicarboxylic acid. Thus, the fluorinated dial is modified by the chain-extension reaction to form a fluorinated dicarboxylic acid.

Preferably, the reaction of the functionalized fluorinated monomer and cyclic carboxylic acid anhydride takes place in bulk, when reaction mixture is a liquid at reaction temperature, although aprotic solvents may be used, if necessary, wherein the reaction mixture is heated under agitation to a temperature of about 100° C. to about 150° C. for about 3 to about 2.0 hours, at which point the reaction mixture is cooled to room temperature. The reaction can be carried out under an inert atmosphere to prevent oxidative discoloration, such as yellowing, of the resulting product. Additionally, although catalysts are not required, a catalyst may be used to facilitate the reaction, such as butylchlorotin dihydroxide.

In another example of the chain-extension reaction of a fluorinated monomer with a cyclic reactant, a fluorine-containing diol having secondary hydroxyl groups is reacted with a cyclic ester to form a fluorinated diol having primary hydroxyl groups, as shown in the following reaction formula:

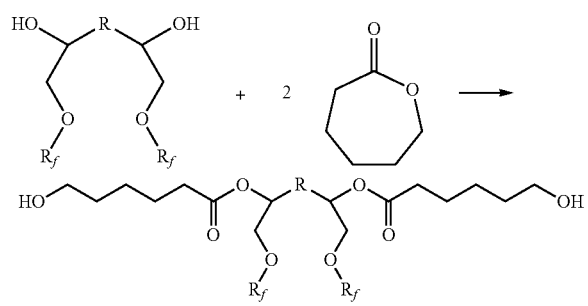

In this reaction, the fluorinated monomer is a fluorinated diol and is reacted with two equivalents of a cyclic ester, ε-caprolactone. The cyclic ester undergoes a ring opening reaction with the hydroxyl groups of the diol to form an ester linkage therewith. The resulting monomer comprises ester linkages and primary hydroxyl groups, which are more reactive than the secondary hydroxyl groups of the reactant fluorinated diol. It is possible for more than one equivalent of ε-caprolactone to add to a given hydroxyl group, in which case the resulting product is a distribution of fluorinated diols with slightly different molecular weights.

Preferably, this reaction takes place in bulk, when reaction mixture is a liquid at reaction temperature, although aprotic solvents may be used, if necessary. The reaction mixture is heated with agitation under an inert atmosphere to a temperature of about 120° C. to about 180° C. for about 3 to about 20 hours, at which point the reaction mixture is cooled to room temperature, A catalyst is used to facilitate the reaction, such as butyltin tris-2-ethylhexanoate.

In another example of the chain-extension reaction of a fluorinated monomer with a cyclic reactant, a fluorine-containing diol having secondary hydroxyl groups is reacted with a cyclic ether to form a propoxylated fluorinated diol, as shown in the following reaction formula:

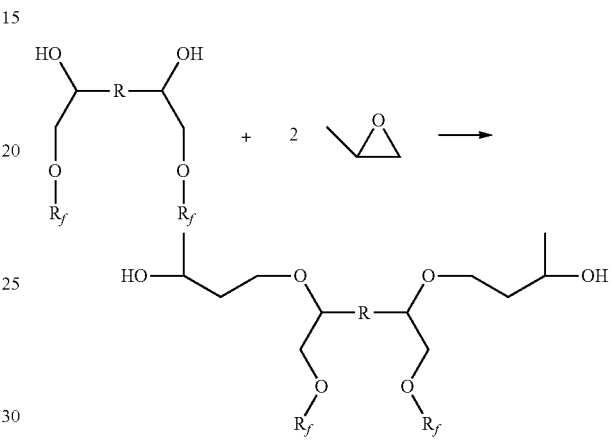

In this reaction, the fluorinated monomer is a fluorinated diol and is reacted with two equivalents of a cyclic ether, propylene oxide. The cyclic ether undergoes a ring-opening reaction with the hydroxyl groups of the diol to form an ether linkage therewith. The resulting chain-extended monomer comprises ether linkages and secondary hydroxyl groups. It is possible for more than one equivalent of propylene oxide to add to a given hydroxyl group, in which case the resulting product is a distribution of fluorinated diols with slightly different molecular weights.

Preferably, the reaction of the fluorinated monomer and the cyclic ether takes place in bulk, with the reaction mixture as a liquid at reaction temperature. In this example, the hydroxy-functional fluorinated diol is heated in the presence of a base catalyst, such as potassium hydroxide, with agitation under an inert atmosphere in a pressure vessel to a temperature of about 80° C. to about 120° C. The propylene oxide charge is then gradually fed to the reactor, maintaining the pressure at about 20 to about 30 psig, over a period of about 1 to about 4 hours, after which, the reaction mixture is cooled to room temperature.

From these examples of chain-extension reactions, it can be seen that various other similar chain-extension reactions can occur using different fluorinated monomers and cyclic reactants that are consistent with the present invention and are readily apparent.

The present invention further includes polymers and/or oligomers made by polymerizing and/or oligomerizing a functionalized fluorinated monomer having at least one hydroxyl group made by any of the methods recited herein, to form a fluorinated polymer. Examples of the various oligomers and polymers that these hydroxy-functional fluorinated monomers and their corresponding hydroxy-functional chain-extended analogues are useful in producing include fluorine-containing polyester, polyether, and polycarbonate polyols, among others.

The fluorine-containing polyester polyols of the present invention can be synthesized via condensation polymerization. In this aspect of the invention, any of the hydroxy-functional, hydroxy-functional chain-extended, carboxylic acid functional, or carboxylic acid functional chain-extended fluorinated monomers of the invention, as described previously, may be used. Generally, the fluorinated monomer or chain-extended fluorinated monomer, along with a mixture of one or more polycarboxylic acids and/or cyclic carboxylic acid anhydrides and one or more polyols, are heated with agitation in the presence of a catalyst under an inert atmosphere to a temperature of about 160° C. to about 250° C. The volatile byproduct of the reaction, in this case water, is removed and collected until the desired extent of reaction is achieved.

Suitable polycarboxylic acids and polycarboxylic acid anhydrides for use in the condensation polymerization reaction include, but are not limited to adipic acid; azelaic acid; sebacic acid; terephthalic acid; isophthalic acid; succinic anhydride; maleic anhydride; phthalic anhydride; 1,4-cyclohexanedicarboxylic acid; hexahydrophthalic anhydride; and trimellitic anhydride. Additionally, the corresponding methyl esters of polycarboxylic acids may be substituted, in which case the polymerization reaction proceeds via transesterification and the volatile byproduct is methanol. Monofunctional carboxylic acids and their methyl esters, such as benzoic acid and saturated and unsaturated fatty acids and their esters may also be included.

Suitable polyols for the condensation polymerization reaction include, but are not limited to ethylene glycol; propylene glycol; diethylene glycol; dipropylene glycol; triethylene glycol; glycerine; diglycerol; butylene glycol; 2-methyl-1,3-propanediol; 2,2-dimethyl-1,3-propanediol; 1,6-hexanediol, 2,4-trimethyl-1,3-pentanedial; trimethylolethane; trimethylolpropane; 1,4-cyclohexanedimethanol; ditrirnethylolpropane; and pentaerythritol.

The fluorine-containing polyester polyols and fluorinated polycarbonate polyols of the present invention can also be synthesized from the hydroxy-functional fluorinated monomers of the present invention and their hydroxy-functional chain-extended analogues, via ring opening polymerization of cyclic esters or cyclic carbonates. The process is virtually the same as described above pertaining to the chain-extension reactions of hydroxy-functional fluorine-containing monomers of the invention, differing only in the ratio of cyclic ester or cyclic carbonate to fluorinated monomer, e.g., the higher the ratio of cyclic ester or cyclic carbonate to fluorinated monomer, the higher the molecular weight of the resulting polyester polyol or polycarbonate polyol.

A functionalized fluorinated monomer having one or more hydroxyl groups can also be reacted with a cyclic ether via ring opening polymerization to form a polyether polyol. As in the case of the ring opening polymerization of cyclic esters, described above, the molecular weight of the resulting polyether polyol increases as the ratio of cyclic ether to fluorinated monomer increases. The polymerization can proceed via an anionic or cationic mechanism, depending on the initiator and conditions chosen. A thorough description of the ring opening polymerization of cyclic ethers and esters can be found in Odian, G., "Principles of Polymerization," 4$^{th}$ Edition, 2004, John Wiley & Sons, Inc., pages 544-618, incorporated herein in relevant part.

The fluorine-containing polycarbonate polyols of the present invention can be synthesized via condensation polymerization by any of several methods. In general, the synthesis is analogous to the synthesis of the fluorine-containing polyester polyols of the invention described above, except that phosgene or any of various dialkyl carbonates are substituted for the polycarboxylic acids and/or cyclic carboxylic acid anhydrides. A thorough description of the synthesis of aromatic polycarbonates from bisphenols and either phosgene or diphenyl carbonate, as well as other methods, can be found in Brunelle, D. J., Korn, M. A., Editors, "Advances in Polycarbonates," 2005, ACS Symposium Series, pages 8-21. A review of the synthesis of aliphatic polycarbonates using various methods, including via transesterification of dialkyl carbonates, is given in J. Appl. Polym. Sci. 2014 Mar. 5; 131(5). Each of these documents are incorporated herein in relevant part.

The fluorine-containing polyester, polyether, and polycarbonate polyols of the present invention can be used to make coatings with improved surface properties, such as graffiti-resistance, stain-resistance, self-cleaning ability, hardness and transparency. The hydroxyl groups on the fluorine-containing polyols can be used to cure such coatings by reacting them with isocyanates and amino resins, for example. The use of polyols in coating formulations in such applications is well known in the art. A thorough description of the chemistry and formulation of such polyol-containing coatings is given in Müller, B., Ulrich, P., "Coatings Formulation: An International Textbook," 2$^{nd}$ Revised Edition, 2011, Hanover: Vincentz Network, pages 98-159, 196-230 and 235-241, which is incorporated herein in relevant part.

The fluorine-containing polyols of the present invention may also contain unsaturation for cross-linking by another mechanism such as copolymerization with ethylenically unsaturated monomers.

In another embodiment of the present invention, the present invention provides a method for making a polyamino-functionalized fluorinated monomer by reacting an unsaturated fluorinated monomer with a polyamine to form a polyamino-functional fluorinated monomer.

The unsaturated fluorinated monomer may be made by a method described herein, or may be any of a number of commercially available unsaturated fluorinated monomers. Suitable commercially available unsaturated fluorinated monomers include, but are not limited to 2,2,2-trifluoroethyl acrylate; 2,2,2-trifluoroethyl methacrylate; 2,2,3,3,3-pentafluoro-1-propyl acrylate; 2,2,3,3,3-pentafluoro-1-propyl methacrylate; 1,1,1,3,3,3-hexafluoroisopropyl acrylate; 1,1,1,3,3,3-hexafluoroisopropyl methacrylate; 2,2,3,3,4,4,4-heptafluoro-1-butyl acrylate; 2,2,3,3,4,4,4-heptafluoro-1-butyl methacrylate; 3,3,4,4,5,5,6,6,7,7,8,8-tridecafluoro-1-octyl acrylate or 3,3,4,4,5,5,6,6,7,7,8,8-tridecafluoro-1-octyl methacrylate. In a preferred embodiment, the unsaturated fluorinated monomer is 2,2,2-trifluoroethyl methacrylate or 3,3,4,4,5,5,6,6,7,7,8,8-tridecafluoro-1-octyl methacrylate.

Suitable polyamines include, but are not limited to 1,2-diaminoethane, 1,2-diaminopropane, 1,3-diaminopropane, 1,4-diaminobutane, 1,5-diaminopentane, 1,6-diaminohexane, 2-methyl-1,5-diaminopentane, 2,5-diamino-2,5-dimethylhexane, 2,2,4-and/or 2,4,4-trimethyl-1,6-diaminohexane, 1,11-diaminoundecane, 1,12-diaminododecane, diethylenetriamine, triethylenetetramine, tetraethylenepentamine, 5-amino-1,3,3-trimethylcyclohexanemethylamine, 2,4'-and/or 4,4'-diaminodicyclohexylmethane, 3'-dimethyl-4,4'-diaminodicyclohexyl methane, 3,3',5,5'-tetramethyl-4,4'-diaminodicyclohexylmethane, 2,2',3,3'-tetramethyl-4,4'-diaminodicyclohexylmethane, 2,4-and/or 2,6-hexahydrotoluene diamine, 2,4 and/or 2,6-diaminotoluene, 2,4' and/or 4,4'-diaminodiphenyl methane and polyether polyamines. In a preferred embodiment, the polyamine is selected from 1,6-diaminohexane, 2-methyl-1,5-diaminopentane, 4,4'-diaminodicyclohexylmethane and 3,3'-dimethyl-4,4'-diaminodicyclohexylmethane.

The reaction of the unsaturated fluorinated monomer with a polyamine takes place via the Michael Addition reaction, wherein the carbon-carbon double bond of the unsaturated fluorinated monomer becomes a carbon-carbon single bond and a new carbon-nitrogen bond is made between the carbon of the monomer and a nitrogen of the polyamine. Thus, the reaction provides a polyamino-functional fluorinated monomer. The resulting fluorinated monomer having amine groups is useful in polyaspartic ester systems for coatings applications.

While various unsaturated fluorinated monomers may be reacted with numerous diamines or polyamines, the following reaction serves as a representative example:

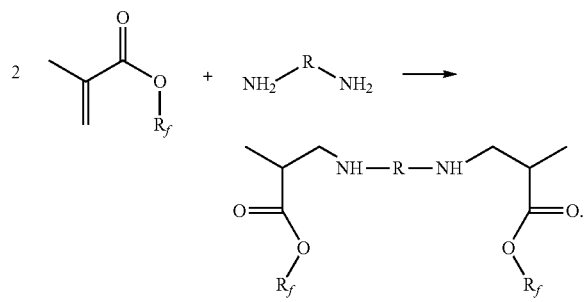

In the above reaction, an unsaturated fluorinated monomer is reacted with a di amine in a 2:1 molar ratio. The amine groups of the diamine each react with the unsaturated, carbon-carbon double bond of the fluorinated monomer via Michael Addition to form a chain-extended fluorinated monomer having di-amino functionality. Preferably, the reaction mixture is heated to maintain the temperature in the range of about 40° C. to about 80° C. for a period of about 2 to about 6 hours.

The present invention further provides chain-extended functionalized fluorinated monomers made by the chain-extension methods recited herein. Such monomers include chain-extended functionalized fluorinated monomers made by reacting a functionalized fluorinated monomer made by a method recited herein with a cyclic reactant. Such chain-extended monomers may have various functional groups depending upon the fluorinated monomer and cyclic reactant used in the reaction. Additionally, chain-extended functionalized fluorinated monomers include polyamino-functional fluorinated monomers made by the method of reacting an unsaturated fluorinated monomer with a polyamine. These chain-extended functionalized fluorinated monomers include polyamine functionality.

Also provided are compositions for making chain-extended functionalized fluorinated monomers including a functionalized fluorinated monomer and a cyclic reactant. The cyclic reactant may be any of a cyclic ether, a cyclic ester, or a cyclic carboxylic acid anhydride.

The present invention further provides compositions for making a polyamino-functional fluorinated monomer, including an unsaturated fluorinated monomer and a polyamine. The polyamino-functional fluorinated monomers of the invention can be reacted with polyisocyanates via condensation polymerization to form a fluorinated polyureas. Additionally, the polyamino-functional fluorinated monomers of the invention can be used in combination with conventional polyaspartic esters in compositions that can be cured with polyisocyanates to form fluorinated polyurea coatings. An overview of the chemistry of polyaspartic ester based polyurea coatings is given in JPCL; 2002 August; 42-47, which is incorporated herein in relevant part.

In another embodiment of the invention, functionalized fluorinated monomers of the invention containing reactive functional groups, including but not limited to hydroxyl, carboxylic acid, amino, epoxide and carboxylic acid anhydride groups and the like, as described previously, can be used to modify existing polymers or oligomers via reaction with functional groups present in the form of end groups or functional groups present on the polymer backbone.

Functionalized fluorinated monomers of the invention containing hydroxyl groups can be reacted with carboxylic acid groups, cyclic carboxylic acid anhydride and isocyanate groups, among others, present on existing polymers or oligomers. In a preferred embodiment, existing polymers containing cyclic anhydride groups derived from maleic anhydride, such as free radically polymerized copolymers of maleic anhydride with styrene, methyl methacrylate, butadiene or ethylene, among others, can be modified by reacting the cyclic anhydrides with the hydroxy-functional fluorinated monomers of the invention. In another preferred embodiment, existing polymeric and oligomeric polyisocyanates, such as trimers of hexamethylene diisocyanate, for example, can be modified by reacting the isocyanates with the hydroxy-functional fluorinated monomers of the invention.

Functionalized fluorinated monomers of the invention containing carboxylic acid groups can be reacted with hydroxyl and epoxide groups, among others, present on existing polymers or oligomers. In a preferred embodiment, polymers containing pendant epoxide groups, such as copolymers containing acrylate or glycidyl methacrylate, for example, can be modified by reacting the epoxide groups with the carboxylic acid-functional fluorinated monomers of the invention. In another preferred embodiment, polymeric and oligomeric epoxy resins, such as polymers and oligomers of bisphenol A diglycidyl ether, for example, can be modified by reacting the epoxides with the carboxylic acid-functional fluorinated monomers of the invention.

Functionalized fluorinated monomers of the invention containing amino groups can be reacted with epoxide, cyclic carboxylic acid anhydride and isocyanate groups, among others, present on existing polymers or oligomers. In a preferred embodiment, existing polymers containing cyclic anhydride groups derived from maleic anhydride, such as free radically polymerized copolymers of maleic anhydride with styrene, methyl methacrylate, butadiene or ethylene, among others, can be modified by reacting the cyclic anhydrides with the amino-functional fluorinated monomers of the invention. In another preferred embodiment, existing polymeric and oligomeric polyisocyanates, such as trimers of hexamethylene diisocyanate, for example, can be modified by reacting the isocyanates with the amino-functional fluorinated monomers of the invention. In a third preferred embodiment, polymers containing pendant epoxide groups, such as copolymers of glycidyl acrylate or methacrylate, for example, can be modified by reacting the epoxide groups with the amino-functional fluorinated monomers of the invention. In a fourth preferred embodiment, polymeric and oligomeric epoxy resins, such as polymers and oligomers of bisphenol A diglycidyl ether, for example, can be modified by reacting the epoxides with the amino-functional fluorinated monomers of the invention.

Functionalized fluorinated monomers of the invention containing epoxide groups can be reacted with hydroxyl, amino and carboxylic acid groups, among others, present on existing polymers or oligomers. In a preferred embodiment, polymers containing pendant carboxylic acid groups, such as polymers and copolymers containing acrylic acid or methacrylic acid, for example, can be modified by reacting the carboxylic acids with the epoxy-functional fluorinated monomers of the invention. In another preferred embodiment, polyesters with carboxylic acid end groups, such as polyethylene terephthalate (PET), for example, can be modified by reacting the carboxylic acid end groups with the epoxy-functional fluorinated monomers of the invention. In a third preferred embodiment, polyamides with amino and carboxylic acid end groups, such as Nylon 6,6, for example, can be modified by reacting the amino and carboxylic acid end groups with the epoxy-functional fluorinated monomers of the invention. In a particularly preferred embodiment, the reaction between the polyamide or polyester end groups and the epoxy-functional fluorinated monomers of the invention takes place via a reactive extrusion process, whereby a composition containing the polymer to be modified and the epoxy-functional fluorinated monomer is fed to an extruder and the reaction takes place in the melt therein, with the modified polymer product exiting the extruder.

Functionalized fluorinated monomers of the invention containing carboxylic acid anhydride groups can be reacted with hydroxyl and amino groups, among others, present on existing polymers or oligomers. In a preferred embodiment, polymers containing pendant hydroxyl groups, such as polyvinyl alcohol, for example, can be modified by reacting the hydroxyl groups with the carboxylic acid anhydride-functional fluorinated monomers of the invention. In another preferred embodiment, polyesters with hydroxyl end groups, such as polyethylene terephthalate (PET), for example, can be modified by reacting the hydroxyl end groups with the carboxylic acid anhydride-functional fluorinated monomers of the invention. In a third preferred embodiment, polyamides with amino end groups, such as Nylon 6,6, for example, can be modified by reacting the amino end groups with the carboxylic: acid anhydride-functional fluorinated monomers of the invention. In a particularly preferred embodiment, the reaction between the polyamide or polyester end groups and the carboxylic acid anhydride-functional fluorinated monomers of the invention takes place via a reactive extrusion process, whereby a composition containing the polymer to be modified and the carboxylic acid anhydride-functional fluorinated monomer is fed to an extruder and the reaction takes place in the melt therein, with the modified polymer product exiting the extender.

The invention will now be described with respect to the following non-limiting examples.

EXAMPLE 1

Reaction of a Fluorinated Alcohol and an Epoxide

A 500 ml 4-necked flask was equipped with a heating mantle, an agitator shaft, a thermocouple, a reflux condenser, and a RUE stopper. The flask was charged with 100.3 grams of 2,2,2-trifluoroethanol and 147.7 grams of cyclohexane dimethanol diglycidyl ether (Epodil® 757 available from Air Products, Inc.). A 6.3111 gram portion of 40% potassium hydroxide solution in water was added dropwise to the reaction mixture with agitation. The reaction mixture was gradually heated to 80° C. and the temperature was maintained in the range of 80-90° C. for a total of 16 hours. After cooling to room temperature, a 219.2 gram portion of the crude product was filtered to remove solids, yielding 213.6 grams of straw colored, transparent liquid product containing the desired 2,2,2-trifluoroethoxy substituted cycloaliphatic polyol product. The complete conversion of the epoxide groups was verified using Fourier Transform Infrared Spectroscopy (FTIR). Subsequent analysis indicated that the product contained 94.23% non-volatile material.

EXAMPLE 2

Reaction of a Fluorinated Alcohol and an Epoxide

A 500 ml 4-necked flask was equipped with a heating mantle, an agitator shaft, a thermocouple, a reflux condenser, and a PTFE stopper. The flask was charged with 99.0 grams of 2,2,2-trifluoroethanol and 145.5 grams of cyclohexane dimethanol diglycidyl ether (Epodil® 757 available from Air Products, Inc.). A 5.4545 grain portion of 22.3% potassium hydroxide solution in methanol was added dropwise to the reaction mixture with agitation. The reaction mixture was gradually heated to 80° C. and the temperature was maintained in the range of 80-85° C. After 21 hours, the complete conversion of epoxide groups was verified via FTIR. A Dean-Stark trap and a nitrogen sparge tube were added. Unreacted 2,2,2-trifluoroethanol and methanol were removed via distillation (3.8 grams). After cooling to room temperature, a portion of the crude product was filtered to remove solids, resulting in 130.4 grams of straw colored, transparent liquid product containing the desired 2,2,2-trifluoroethoxy substituted cycloaliphatic polyol product. Analysis of the product indicated a hydroxyl number of 257.1 (mg KOH/g) and a base number of 0.0 (mg KOH/g), which verified the complete removal of potassium hydroxide by the filtration. The remaining 93.8 grams of crude product was diluted with 23.5 grams of n-butyl acetate and filtered to remove solids, resulting in 113.3 grams of solution containing approximately 80% of the desired 2,2,2-trifluoroethoxy substituted cycloaliphatic polyol product.

EXAMPLE 3

Reaction of a Fluorinated Alcohol and an Epoxide

A 500 ml 4-necked flask was equipped with a heating mantle, an agitator shaft, a thermocouple, a reflux condenser, and a PTFE stopper. The flask was charged with 141.8 grams of 2,2,2-trifluoroethanol and 207.7 grams of cyclohexane dimethanol diglycidyl ether (Epodil® 757 available from Air Products, Inc.). A 8.1015 gram portion of 22.3% potassium hydroxide solution in methanol was added dropwise to the reaction mixture with agitation. The reaction mixture was gradually heated to 80° C. and the temperature was maintained in the range of 80-85° C. After 21 hours, the complete conversion of epoxide groups was verified via FUR, and reaction mixture was cooled. Unreacted 2,2,2-trifluoroethanol and methanol were removed via rotary evaporator (10.2 grams), yielding 330.5 grams of crude product. The crude product was diluted with 82.6 grams of n-butyl acetate and solids were removed using vacuum filtration. Analysis of the base number of the filtered product (0.0 mg KOH/g) verified the complete removal of potassium hydroxide by the filtration. The synthesis yielded 330.4 grams of a straw colored, transparent product solution containing the desired 2,2,2-trifluoroethoxy substituted cycloaliphatic polyol. Analysis of the product solution indicated it contained 89.97% non-volatile material.

EXAMPLE 4

Reaction of a Fluorinated Alcohol and an Epoxide

A 500 ml 4-necked flask was equipped with a heating mantle, an agitator shaft, a thermocouple, a reflux condenser, and a PTFE stopper. The flask was charged with 32.8 grams of 4-hydroxyphenylsulfur pentafluoride, 24.2 grams of cyclohexane dimethanol diglycidyl ether (Epodil® 757 available from Air Products, Inc.), and 57.0 grams of methyl ethyl ketone (MEK). A 2.5043 gram portion of 22.3% potassium hydroxide solution in methanol was added dropwise to the reaction mixture with agitation. The reaction mixture was gradually heated to 80° C. and the temperature was maintained in the range of 80-85° C. After 17 hours, the complete conversion of epoxide groups was verified via FTIR and the reaction mixture was cooled. After removal of a 6.2 gram sample, residual potassium hydroxide in the remaining crude product was neutralized via dropwise addition of 1.2 grams of 37% hydrochloric acid. The resulting neutralized product solution was filtered to remove solids (0.7 grams). An additional 12.3 grams of MEK was used to transfer product from reaction flask to filter and wash filter cake. The synthesis yielded 112.5 grams of a straw-colored, transparent product solution containing the desired 4-pentafluorosulfurphenoxy substituted cycloaliphatic polyol. Analysis of the product solution indicated it contained 40.91% non-volatile material.

EXAMPLE 5

Reaction of a Fluorinated Alcohol and an Epoxide

A 500 ml 4-necked flask was equipped with a heating mantle, an agitator shaft, a thermocouple, a reflux condenser, and a PTFE stopper. The flask was charged with 153.9 grams of pentaerythritol tetraglycidyl ether (Erisys® GE-40 available from Emerald Performance Materials, Inc.) and 46.2 grams (0.5 equivalents) of 2,2,2-trifluoroethanol. A 4.7691 gram portion of 22.3% potassium hydroxide solution in methanol was added dropwise to the reaction mixture with agitation. The reaction mixture was gradually heated to 80° C. and the temperature was maintained in the range of 80-85° C. After 4 hours, analysis via FUR verified the complete consumption of 2,2,2-trifluoroethanol and the conversion of 59.8% of the epoxide groups to ether linkages, after which, the reaction mixture was cooled. The crude product was diluted with MEK and solids were removed using vacuum filtration. A total of 67.3 grams of MEK was added, including the amount used to wash product out of the reaction flask and rinse the filter cake. The resulting 240.5 grams of transparent, straw colored product solution was stripped to remove MEK and methanol via rotary evaporator. The synthesis yielded 196.7 grams of a viscous, straw colored, transparent liquid containing the desired 2,2,2-trifluoroethoxy substituted epoxy-functional polyol product. Analysis of the base number of the final product (0.0 mg KOH/g) verified the complete removal of potassium hydroxide by the filtration. The calculated epoxy equivalent weight of the product was 540.5 grams/equivalent.

EXAMPLE 6

Reaction of Fluorinated Monomer with Cyclic Ester

A 500 ml 4-necked flask was equipped with a heating mantle, an agitator shaft, a thermocouple, a reflux condenser, and a PTFE stopper. The flask was charged with 100.0 grams of the undiluted product from Example 2 and 52.4 grams of ε-caprolactone. The reaction mixture was heated to 153° C. with agitation and 0.0816 grams of butyltin tris-2-ethylhexanoate was added dropwise. The reaction mixture was heated to maintain the temperature in the range of 160-165° C. After 16.5 hours, the reaction mixture was cooled to yield 147.4 grams of a straw-colored, transparent liquid containing the desired chain extended 2,2,2-trifluoroethoxy substituted cycloaliphatic polyol product.

EXAMPLE 7

Reaction of Fluorinated Monomer and a Cyclic Anhydride

A 500 ml 4-necked flask was equipped with a heating mantle, an agitator shaft, a thermocouple, a reflux condenser, and a PTFE stopper. The flask was charged with 100.0 grams of the 90% product solution in n-butyl acetate from Example 3 and 61.5 grams of hexahydrophthalic anhydride. The reaction mixture was heated and, after exotherm to 150° C. subsided, the temperature was maintained in the range of 120-125° C. with agitation. After 3.3 hours, the reaction mixture was cooled to yield 151.6 grams of a viscous, straw-colored, transparent liquid containing the desired chain extended 2,2,2-trifluoroethoxy substituted cycloaliphatic polyol product. Comparison of methanolysis and hydrolysis acid numbers indicated a 98.1% conversion of anhydride moieties to the desired fluorinated alcohol derived esters.

EXAMPLE 8

Reaction of Fluorinated Monomer and a Cyclic Anhydride

A 500 ml 4-necked flask was equipped with a heating mantle, an agitator shaft, a thermocouple, a reflux condenser, and a nitrogen sparge tube. The flask was charged with 100.0 grams of the 41% product solution in MEK from Example 4, 21.3 grams of hexahydrophthalic anhydride, and 0.0971 grams of butylchlorotin dihydroxide. A 5.0 gram portion of MEK was used to wash residual reactants from the charging funnel into the reaction flask. The reaction mixture was heated and, after a mild exotherm subsided, the temperature was maintained in the range of 80-85° C. with agitation. After 17 hours, the reaction mixture was cooled to yield 124.4 grams of a straw-colored, transparent liquid containing the desired chain extended 4-pentafluorosulfurphenoxy substituted cycloaliphatic polyol product. Comparison of methanolysis and hydrolysis acid numbers indicated a 96.6% conversion of anhydride moieties to the desired fluorinated alcohol derived esters.

EXAMPLE 9

Polymerization of Fluorinated Monomer

A 4,000 ml reaction flask having a 4-necked head was equipped with a heating mantle, an agitator shaft, a thermocouple, a nitrogen sparge tube, a Vigreux column, a condenser and a receiver. The reaction flask was charged with 949.8 grams of hexahydrophthalic anhydride, 1,577.1 grams of trimethylolpropane, 608.4 grams of phthalic anhydride, 119.4 grams of the product from Example 7 and 1.5882 grams of butylstannoic acid. The reaction mixture was gradually heated with nitrogen sparge and agitation to a temperature of 210° C. over the course of 3.75 hours. The temperature was maintained in the range of 210-215° C. with agitation for an additional 17.25 hours, at which time the Vigreux column was removed and the reaction was continued until the expected amount of total condensate was collected, an additional 7 hours. The reaction mixture was cooled to 140° C. and the resulting polyester resin was diluted by gradually adding 1,442.8 grams of propylene glycol monomethyl ether acetate with agitation. The reaction yielded 4,323.4 grams of polyester polyol product solution in the form of a light colored, transparent liquid. The polyester solution was analyzed and found to have a hydroxyl number of 165.6 (mg KOH/g), an acid number of 2.60 (mg KOH/g), 69,96% non-volatile material, a Gardner-Holdt viscosity of Z6+ at 417 seconds, a density of 9.45 pounds per gallon, and a Gardner color of less than 1. The calculated fluorine content of the undiluted polyester resin was 0.5%.

EXAMPLE 10

Polymerization of Fluorinated Monomer

A 500 ml 4-necked reaction flask was equipped with a heating mantle, an agitator shaft, a thermocouple, a nitrogen sparge tube, and a reflux condenser. The reaction flask was charged with 96.2 grams of hexahydrophthalic anhydride and 16.2 grams of the product from Example 8. The reaction mixture was heated and the temperature was maintained in the range of 80-85° C. with agitation. After 2 hours, 160.7 grams of trimethylolpropane, 61.5 grams of phthalic anhydride, and 0.1638 grams of butylstannoic acid were charged and a Dean-Stark trap and insulation were added. The reaction mixture was gradually heated with nitrogen sparge and agitation to a temperature of 210° C. over the course of 3.75 hours. The temperature was maintained in the range of 210-215° C. with agitation until the expected amount of total condensate was collected, an additional 22.5 hours. The reaction mixture was cooled to 140° C. and the resulting polyester resin was diluted by gradually adding 141.2 grams of propylene glycol monomethyl ether acetate with agitation. The reaction yielded 423.9 grams of polyester polyol product solution in the form of a light colored, transparent liquid. The polyester polyol product solution was analyzed and found to have a hydroxyl number of 175.9 (mg KOH/g), an acid number of 2.74 (mg KOH/g), 69.90% non-volatile material, a Gardner-Holdt viscosity of Z6+ at 338 seconds, a density of 9.45 pounds per gallon, and a Gardner color of less than 1. The calculated fluorine content of the undiluted polyester resin was 0.5%.

EXAMPLE 11

Polymerization of Fluorinated Monomer

A 2,000 ml 5-necked reaction flask was equipped with a heating mantle, an agitator shaft, a thermocouple, a nitrogen sparge tube, a Vigreux column, a condenser and a receiver. The reaction flask was charged with 800.7 grams of 2-methyl-1,3-propanediol, 931.5 grams of dimethyl carbonate, 2.9 grams of 1.0 N KOH solution in methanol, and 24.2 grams of the product from Example 3, after n-butyl acetate was removed via rotary evaporator. The reaction mixture was gradually heated with nitrogen sparge and agitation to a temperature of 80-85° C. and held for 16 hours. The temperature was then raised in ten degree increments and held at each temperature until the temperature at the top of the column fell below 60° C., and until a final temperature in the range of 170-175° C. was reached, after an additional 8.75 hours. Condensate, consisting of methanol and dimethyl carbonate, was continuously collected and analyzed via refractometer to determine the methanol content of the condensate, After the expected amount of methanol was collected, the reaction mixture was cooled to 40° C. and the resulting polycarbonate resin was isolated, with a yield of 1,016.4 grams of product in the form of a light colored, transparent liquid. The polycarbonate product was analyzed and found to have a hydroxyl number of 284.6 (mg KOH/g), an acid number of 0.12 (mg KOH/g), a Brookfield viscosity of 2,000 centipoise at 25° C., a density of 9.66 pounds per gallon and a. Gardner color of less than 1. The calculated fluorine content of the polycarbonate resin was 0.5%.

EXAMPLE 12

Reaction of Fluorinated Alcohol with Cyclic Anhydride

A 500 ml 4-necked flask was equipped with a heating mantle, an agitator shaft, a thermocouple, a nitrogen sparge tube, and a reflux condenser. The flask was charged with 163.4 grams of 3,3,4,4,5,5,6,6,7,7,8,8-tridecafluoro-1-octanol and 89.8 grams of 1,2,4-cyclohexanetricarboxylic anhydride. The reaction mixture was heated to 125° C. with agitation and nitrogen purge. After exotherm 164° C. subsided, the temperature was maintained in the range between 120° C. and 125° C. for 5.5 hours. The resulting product was isolated while hot in the form of a high viscosity, clear, colorless liquid containing the desired 3,3,4,4,5,5,6,6,7,7,8, 8,8-tridecafluoro-1-octyl monoester of 1,2,4-cyclohexanetricarboxylic acid with a yield of 243.8 grams. Upon cooling to room temperature, product crystallized and formed an opaque white solid. Comparison of methanolysis and hydrolysis acid numbers indicated a 96.8% conversion of anhydride moieties to the desired fluorinated alcohol derived esters.

EXAMPLE 13

Reaction of Fluorinated Alcohol with Cyclic Anhydride

A 500 ml 4-necked flask was equipped with a heating mantle, an agitator shaft, a thermocouple, a reflux condenser, and a PTFE stopper. The flask was charged with 57.0 grams of 2,2,2-trifluoroethanol, 72.5 grams of trimellitic anhydride, and 0.0874 grams of butylchlorotin dihydroxide. The reaction mixture was heated to maintain temperature in the range of 70-30° C. with agitation and 2,2,2-trifluoroethanol reflux. When the reaction mixture thickened significantly, 18.8 grams of 2,2,2-trifluoroethanol was added. After 23 hours, a Dean-Stark trap was added and unreacted 2,2,2-trifluoroethanol was removed via distillation (47.4 grams). The product, in the form of a white solid, was dispersed with the addition of 51.7 grams of methyl ethyl ketone. After isolating the product slurry, the solvent was evaporated to yield 104.9 grams of the desired 2,2,2-trifluoroethyl monoester of 1,2,4-benzenetricarboxylic acid product in the form of a white solid. Comparison of methanolysis and hydrolysis acid numbers indicated 96.0% conversion of anhydride moieties to the desired fluorinated alcohol derived esters.

EXAMPLE 14

Reaction of Fluorinated Alcohol with Cyclic Anhydride

A 500 ml 4-necked flask was equipped with a heating mantle, an agitator shaft, a thermocouple, a reflux condenser, and a PTFE stopper. The flask was charged with 131.4 grams of 2,2,2-trifluoroethanol, 135.5 grams of hexahydrophthalic anhydride, and 0.1718 grams of butylchlorotin dihydroxide. The reaction mixture was heated to maintain the temperature in the range of 80-90° C. with agitation and 2,2,2-trifluoroethanol reflux. After 18.75 hours, a Dean-Stark trap was added and unreacted 2,2,2-trifluoroethanol was removed via distillation (41.9 grams). The desired 2,2,2-trifluoroethyl monoester of hexahydrophthalic acid product of the reaction was isolated in the form of a straw-colored liquid with a yield of 209.1 grams. Comparison of methanolysis and hydrolysis acid numbers indicated 92.6% conversion of anhydride moieties to the desired fluorinated alcohol derived esters.

EXAMPLE 15

Reaction of Fluorinated Alcohol with Cyclic Anhydride

A 500 ml 4-necked flask was equipped with a heating mantle, an agitator shaft, a thermocouple, a reflux condenser, and a PTFE stopper. The flask was charged with 91.4 grams of 3,3,4,4,5,5,6,6,7,7,8,8,8-tridecafluoro-1-octanol, 24.7 grams of maleic anhydride, and 0.0743 grains of butylchlorotin dihydroxide. The reaction mixture was heated to a temperature of 125° C. with agitation. After exotherm to 155° C. subsided, the temperature was maintained in the range of 120-130° C. for 2.75 hours. The intermediate product of the reaction, containing the desired 3,3,4,4,5,5,6,6,7,7,8,8,8-tridecafluoro-1-octyl monoester of maleic acid, had a hydrolysis acid number of 133.5 (mg KOH/g), and a calculated 90.9% conversion of anhydride moieties to the desired fluorinated alcohol derived esters. A total of 58.6 grams of butyl glycidyl ether (Epodil® 741, available from Air Products, Inc.) was then charged, in three aliquots, over 22.75 hours and the temperature was maintained in the range of 120-130° C. for an additional 17.33 hours. The final product, containing the desired maleate diester, was isolated in the form of an orange/brown liquid, with a yield of 160.6 grams and an acid number of 7.16 (mg KOH/g).

EXAMPLE 16

Reaction of Fluorinated Alcohol with Cyclic Anhydride

A 500 ml 4-necked flask was equipped with a heating mantle, an agitator shaft, a thermocouple, a reflux condenser, and a PTFE stopper. The flask was charged with 99.0 grams of 2,2,2-trifluoroethanol, 48.2 grams of maleic anhydride, and 0.1194 grams of butylchlorotin dihydroxide. The reaction mixture was heated to maintain the temperature in the range of 80-90° C. with agitation and 2,2,2-trifluoroethanol reflux. After 25 hours, a Dean-Stark trap was added and unreacted 2,2,2-trifluoroethanol was removed via distillation (59.6 grams). The intermediate product of the reaction containing the desired 2,2,2-trifluoroethyl monoester of maleic acid was not isolated. A total of 137.9 grams of butyl glycidyl ether (Epodil® 741, available from Air Products, Inc.) was then charged, in two aliquots, over the next 5.50 hours and the temperature was maintained in the range of 120-130° C. for an additional 16.75 hours. The final product, containing the desired maleate diester, was isolated in the form of an orange/brown liquid, with a yield of 207.4 grams and an acid number of 3.93 (mg KOH/g).

EXAMPLE 17

Reaction of Fluorinated Alcohol and Alkyl Halide

A 500 ml 4-necked flask was equipped with a heating mantle, an agitator shaft, a thermocouple, a reflux condenser, and a PTFE stopper. The flask was charged with 55.7 grams of 2,2,2-trifluoroethanol, 56.0 grams of 3-chloro-1,2-propanediol, and 50.3 grams of deionized water. A solution of 38.5 grams of 85% potassium hydroxide dissolved in 100.0 grams of deionized water was gradually charged with agitation by pouring down the reflux condenser. An additional 20.6 grams of deionized water was used to wash any solution left in the condenser into the reaction mixture. After exotherm to 98° C. subsided, the temperature was maintained in the range of 70-75° C. for an additional 15 hours. The resulting solution of crude product (292.8 grams) was transferred to a 1,000 ml round bottom flask, from which water and unreacted 2,2,2-trifluoroethanol were removed using a rotary evaporator (147.9 grams). The resulting 120.8 grams of stripped crude product, containing solid potassium chloride and potassium hydroxide was diluted with 100.0 grams of acetone and filtered to remove solids (36.9 grams). The filtered solution of product in acetone was stripped via the rotary evaporator to yield 83.6 grams of product, containing the desired 3-(2,2,2-trifluoroethoxy)-1,2-propanediol (TFEPD) in the form of a viscous brown liquid.

EXAMPLE 18

Reaction of Fluorinated Alcohol and Alkyl Halide

A 500 ml 4-necked flask was equipped with a heating mantle, an agitator shaft, a thermocouple, a reflux condenser, and a PTFE stopper. The flask was charged with 89.2 grams of 2,2,2-trifluoroethanol and 89.5 grams of 3-chloro-1,2-propanediol. A solution of 61.4 grams of 85% potassium hydroxide dissolved in 130.0 grams of deionized water was gradually charged with agitation by pouring down the reflux condenser. An additional 30.0 grams of deionized water was used to wash any solution left in the condenser into the reaction mixture. After exotherm to 100° C. with water reflux subsided, temperature was maintained in the range of 70-75° C. for an additional 16 hours. After cooling to room temperature, residual potassium hydroxide was neutralized via dropwise addition of 16.6 grams of 37% hydrochloric acid. A 299.5 gram portion of the neutralized product solution was filtered to remove solids (13.0 grams), placed in a separatory funnel, and extracted with 86.2 grams of n-butyl acetate. After removal of the aqueous layer, the resulting product solution containing the desired 3-(2,2,2-trifluoroethoxy)-1,2-propanediol (TFEPD) had a yield of 198.6 grams and a calculated composition of 51.9% TFEPD, 43.4% n-butyl acetate, and 4.7% water (via Karl Fischer coulometric titration).

EXAMPLE 19

Reaction of Fluorinated Alcohol and Alkyl Halide

A 500 ml 4-necked flask was equipped with a heating mantle, an agitator shaft, a thermocouple, a reflux condenser, and a pressure equalizing addition funnel. The flask was charged with 123.0 grams of 2,2,2-trifluoroethanol and 123.6 grams of 3-chloro-1,2-propanediol. A solution of 153.5 grams of 40% potassium hydroxide in water was added dropwise to minimize exotherm. An additional 19.6 grams of deionized water was used to wash any solution left in the addition funnel into the reaction mixture. After exotherm to 100° C. with mild water reflux subsided, the temperature was maintained in the range of 70-75° C. for an additional 16 hours. After cooling to room temperature, residual potassium hydroxide was neutralized via dropwise addition of 13.4 grams of 37% hydrochloric acid. After filtration to remove solids (54.4 grams), the resulting clear aqueous product solution (336.7 grams) was placed in a separatory funnel and extracted with 105.6 grams of methyl amyl ketone. After removal of the aqueous layer, the resulting product solution (375.0 grams) was dried over magnesium sulfate and filtered to yield 211.0 grams of product solution with a calculated composition of 53% TFEPD and 47% methyl amyl ketone.

EXAMPLE 20

Reaction of Fluorinated Monomer and Cyclic Anhydride

A 500 ml 4-necked flask was equipped with a heating mantle, an agitator shaft, a thermocouple, a reflux condenser, and a PTFE stopper. The flask was charged with 100.0 grams of the product solution from Example 19, 93.8 grams of hexahydrophthalic anhydride, and 0.1543 grams of butylchlorotin dihydroxide. The reaction mixture was heated and, after exotherm to 150° C. subsided, the temperature was maintained in the range of 120-125° C. with agitation. After 3.5 hours, the reaction mixture was cooled to yield 187.2 grams of product in the form of a light brown, opaque liquid containing the desired 2:1 adduct of hexahydrophthalic anhydride and TFEPD. Comparison of methanolysis and hydrolysis acid numbers indicated a. 99.1% conversion of anhydride moieties to the desired fluorinated alcohol derived esters. Subsequent analysis indicated a composition of 78.9% non-volatile material and 21.1% methyl amyl ketone.

EXAMPLE 21

Polymerization of Fluorinated Monomer

A 4,000 ml reaction flask having a 4-necked head was equipped with a heating mantle, an agitator shaft, a thermocouple, a nitrogen sparge tube, a Vigreux column, a condenser and a receiver. The reaction flask was charged with 917.6 grams of hexahydrophthalic anhydride, 1,564.8 grams of trimethylolpropane, 599.6 grams of phthalic anhydride, 171.1 grams of the product from Example 20, and 1.5656 grams of butylstannoic acid. The reaction mixture was gradually heated with nitrogen sparge and agitation to a temperature of 210° C. over the course of 4 hours. The temperature was maintained in the range of 210-215° C. with agitation for an additional 16.7 hours, at which time the Vigreux column was removed and the reaction was continued until the expected amount of total condensate was collected, an additional 6.25 hours. The reaction mixture was cooled to 140° C. and the resulting polyester resin was diluted by gradually adding 1,428.8 grams of propylene glycol monomethyl ether acetate with agitation. The reaction yielded 4,248.7 grams of polyester product solution. A portion of the polyester solution was filtered to remove some insoluble solids, resulting in 1,350.0 grams of a polyester polyol product solution in the form of a light colored, transparent liquid. The filtered product was analyzed and found to have a hydroxyl number of 164.7 (mg KOH/g), an acid number of 2.33 (mg KOH/g), 68.89% non-volatile material, a Gardner-Holdt viscosity of Z6 at 303 seconds, a density of 9.45 pounds per gallon, and a Gardner color of less than 1. The calculated fluorine content of the undiluted polyester resin was 0.5%.

EXAMPLE 22

Reaction of Fluorinated Alcohol and Alkyl Halide

A 500 ml 4-necked flask was equipped with a heating mantle, an agitator shaft, a thermocouple, a reflux condenser, and a pressure equalizing addition funnel. The flask was charged with 117.4 grams of 2,2,2-trifluoroethanol and 139.0 grams of 2,2-bis(bromomethyl)-1,3-propanediol. A solution of 145.8 grams of 40% potassium hydroxide in water was added dropwise to minimize exotherm. An additional 20.8 grams of deionized water was used to wash any solution left in the addition funnel into the reaction mixture. After exotherm to 71° C. subsided, the temperature was maintained in the range of 70-75° C. for an additional 17 hours. An additional 45.3 grams of deionized water was added to dissolve all solids and reaction was cooled. Residual potassium hydroxide was neutralized via dropwise addition of 8.4 grams of 37% hydrochloric acid. The resulting mixture was placed in a separatory funnel, where it split into two phases, with salt precipitating from the lower, aqueous phase. An additional 80.1 grams of deionized water was used to wash residual salts from reaction flask and dissolve all solids in separatory funnel. The upper, organic layer was collected and placed in a 1,000 ml flask, along with 30.0 grams of xylene, to aid in the removal of water via azeotrope. The resulting mixture was stripped to remove water and xylene via rotary evaporator, which yielded 70.3 grams of a liquid product containing the desired 2,2-bis(trifluoroethoxymethyl)-1,3-propanediol (BTFEMPD). Analysis of the product via FTIR indicates 96.0% conversion of alkyl bromides to trifluoroethyl ethers.

EXAMPLE 23 reaction of Fluorinated Monomer and Cyclic Anhydride

A 500 ml 4-necked flask was equipped with a heating mantle, an agitator shaft, a thermocouple, a reflux condenser, and a PTFE stopper. The flask was charged with 38.2 grams of the product solution from Example 22 and 40.1 grams of hexahydrophthalic anhydride. The reaction mixture was heated and, after exotherm subsided, the temperature was maintained in the range of 120-125° C. with agitation. After 3 hours, the reaction mixture was cooled to less than 100° C. and the 78.3 grams of product in the form of a viscous yellow liquid containing the desired 2:1 adduct of hexahydrophthalic anhydride and BTFEMPD was charged directly to the polymerization reaction described below in Example 24, using a small amount of methyl ethyl ketone to rinse the reaction flask to ensure quantitative transfer.

EXAMPLE 24

Polymerization of Fluorinated Monomer

A 4,000 ml reaction flask having a 4-necked head was equipped with a heating mantle, an agitator shaft, a thermocouple, a nitrogen sparge tube, a Vigreux column, a condenser and a receiver. The reaction flask was charged with 909.5 grams of hexahydrophthalic anhydride, 1,507.9 grams of trimethylolpropane, 583.3 grams of phthalic anhydride, 78.3 grams of the product from Example 23 and 1.5198 grams of butylstannoic acid. The reaction mixture was gradually heated with nitrogen sparge and agitation to a temperature of 210° C. over the course of 3.75 hours. The temperature was maintained in the range of 210-215° C. with agitation for an additional 0.75 hours, at which time the Vigreux column was removed and the reaction was continued until the expected amount of total condensate was collected, an additional 20 hours. The reaction mixture was cooled to 140° C. and the resulting polyester resin was diluted by gradually adding 1,360.4 grams of propylene glycol monomethyl ether acetate with agitation. The reaction yielded 4,109.9 grams of polyester product solution light colored, transparent liquid. The polyester polyol product solution was analyzed and found to have a hydroxyl number of 169.2 (mg KOH/g), an acid number of 2.37 (mg KOH/g), 70.24% non-volatile material, a Gardner-Holdt viscosity of Z6+ at 390 seconds, a density of 9.45 pounds per gallon, and a Gardner color of less than 1. The calculated fluorine content of the undiluted polyester resin was 0.5%.

EXAMPLE 25

Synthesis of Fluorinated Tosylate

A 500 ml 4-necked flask was equipped with a heating mantle, an agitator shaft, a thermocouple, a reflux condenser, and a PTFE stopper. The flask was charged with 75.0 grams of p-toluenesulfonyl chloride, 39.8 grams of trimethylamine and 110.2 grams of methyl ethyl ketone. The reaction mixture was stirred and 44.3 grams of 2,2,2-trifluoroethanol was fed dropwise via a pressure equalizing addition funnel fitted to the top of the condenser, followed by an additional 22.9 grams of methyl ethyl ketone to rinse funnel and condenser into reaction flask. After exotherm to 77° C. subsided, the reaction mixture was stirred overnight, an additional 15 hours. The resulting mixture was filtered to remove the insoluble triethylamine hydrochloride salt and stripped to remove methyl ethyl ketone and excess 2,2,2-trifluoroethanol using a rotary evaporator. The final product was isolated in the form of 99.7 grams of a brown liquid containing the desired 2,2,2-trifluoroethyl p-toluenesulfonate, which crystallized upon cooling to ambient temperature.

EXAMPLE 26

Synthesis of Fluorinated Tosylate

A 500 ml 4-necked flask was equipped with a heating mantle, an agitator shaft, a thermocouple, a reflux condenser, and a nitrogen inlet. The flask was charged with 55.2 grams of p-toluenesulfonyl chloride, 29.3 grams of trimethylamine and 170.0 grams of methyl ethyl ketone. The reaction mixture was stirred with a slight nitrogen purge in the headspace and 105.4 grams of 3,3,4,4,5,5,6,6,7,7,8,8,8-tridecafluoro-1-octanol was fed dropwise via a pressure equalizing addition funnel fitted to the top of the condenser, followed by an additional 55.0 grams of methyl ethyl ketone to rinse funnel and condenser into reaction flask. After exotherm to 37° C. subsided, the reaction mixture was stirred overnight, an additional 15 hours. The resulting mixture was filtered to remove the insoluble triethylamine hydrochloride salt and stripped to remove methyl ethyl ketone using a rotary evaporator. The final product was isolated in the form of 145.2 grams of a brown liquid containing the desired 3,3,4,4,5,5,6,6,7,7,8,8,8-tridecafluoro-1-octyl p-toluenesulfonate, which crystallized upon cooling to ambient temperature.

EXAMPLE 27

Reaction of Fluorinated Tosylate with Alcohol via Alkoxide Intermediate

A 500 ml 4-necked flask was equipped with a heating mantle, an agitator shaft, a thermocouple, a reflux condenser, and a nitrogen inlet. The flask was charged with 43.8 grams of dimethyl-5-hydroxyisophthalate, 107.9 grams of the product from Example 26, 43.3 grams of anhydrous potassium carbonate and 202.9 grams of anhydrous acetone. The reaction mixture was stirred with a slight nitrogen purge in the headspace and heated to acetone reflux. The temperature was maintained in the range of 55-57° C. for an additional 17.75 hours. The resulting mixture was filtered to remove excess potassium carbonate and insoluble byproducts and filter cake and flask were rinsed with methyl ethyl ketone. The resulting solution was stripped to remove acetone and methyl ethyl ketone using a rotary evaporator. The final product was isolated in the form of 19.3 grams of a brown liquid containing the desired 3,3,4,4,5,5,6,6,7,7,8,8,8-tridecafluoro-1-octyl ether of dimethyl-5-hydroxyisophthalate, which hardened to a glassy state upon cooling to ambient temperature.

EXAMPLE 28

Polymerization of Fluorinated Monomer

A 4,000 ml reaction flask having a 4-necked head was equipped with a heating mantle, an agitator shaft, a thermocouple, a nitrogen sparge tube, a Vigreux column, a condenser and a receiver. The reaction flask was charged with 545.3 grams of hexahydrophthalic anhydride, 892.2 grams of trimethylolpropane, 349.3 grams of phthalic anhydride, 19.2 grams of the product from Example 27 and 0.8979 grams of butylchlorotin dihydroxide. The reaction mixture was gradually heated with nitrogen sparge and agitation to a temperature of 210° C. over the course of 3.5 hours. The temperature was maintained in the range of 210-215° C. with agitation for an additional 1 hour, at which time the Vigreux column was removed and the reaction was continued until the expected amount of total condensate was collected, an additional 19.25 hours. The reaction mixture was cooled to 140° C. and the resulting polyester resin was diluted by gradually adding 828.7 grams of propylene glycol monomethyl ether acetate with agitation. The reaction yielded 2,424.0 grams of polyester product solution light colored, transparent liquid. The polyester polyol product solution was analyzed and found to have a hydroxyl number of 170.6 (mg KOH/g), an acid number of 3.95 (mg KOH/g), 69.69% non-volatile material, a Gardner-Holdt viscosity of Z6+ at 325 seconds, a density of 9.45 pounds per gallon, and a Gardner color of less than 1. The calculated fluorine content of the undiluted polyester resin was 0.5%.

EXAMPLE 29

Reaction of Fluorinated Tosylate and Amine

A 500 ml 4-necked flask was equipped with a heating mantle, an agitator shaft, a thermocouple, a reflux condenser, and a nitrogen inlet. The flask was charged with 10.0 grams of diethanolamine, 49.4 grams of 3,3,4,4,5,5,6,6,7,7,8,8,8-tridecafluoro-1-octyl p-toluenesulfonate, 26.3 grams of anhydrous potassium carbonate and 150.0 grams of dimethyl formamide. The reaction mixture was stirred with a slight nitrogen purge in the headspace and heated to 115° C. The temperature was maintained in the range of 114-116° C. for an additional 20 hours. The resulting mixture was filtered to remove excess potassium carbonate and insoluble byproducts and filter cake and flask were rinsed with dimethyl formamide and methyl ethyl ketone. The resulting solution was stripped to remove dimethyl formamide and methyl ethyl ketone using a rotary evaporator. The final product was isolated in the form of 28.8 grams of a dark brown viscous liquid containing the desired 3,3,4,4,5,5,6,6,7,7,8,8,8-tridecafluoro-1-octyl diethanolamine.

EXAMPLE 30

Reaction of Fluorinated Monomer with a Polyamine

A 500 ml 4-necked flask was equipped with a heating mantle, an agitator shaft, a thermocouple, a reflux condenser, and a PTFE stopper. The flask was charged with 162.5 grams of 2,2,2-trifluoroethyl methacrylate. A 56.2 gram portion of 2-methylpentane-1,5-diamine was added dropwise to the reaction mixture with agitation. After exotherm to 70° C. subsided, the reaction mixture was heated to maintain the temperature in the range of 50-55° C. After 4 hours, complete conversion of carbon-carbon double bonds was verified via FUR and reaction mixture was cooled to yield 214.4 grams of product containing the desired fluorinated diamine in the form of a straw-colored, transparent liquid.

COMPARATIVE EXAMPLE 1

A 500 ml 4-necked flask was equipped with a heating mantle, an agitator shaft, a thermocouple, a nitrogen sparge tube, and a Dean-Stark trap with a reflux condenser. The flask was charged with 201.4 grams of a partially fluorinated polyether diol with a hydroxy equivalent weight of 1,740 (available from Omnova Solutions under the trade name PolyFox™ PF-6320), 17.8 grams of adipic acid (2.1 equivalents), and 0.2256 grams of butylstannoic acid. The reaction mixture was heated to 210° C. with agitation and nitrogen purge over the course of 1 hour. The temperature was maintained in the range of 210-215° C.; with agitation until the expected amount of total condensate was collected, an additional 18 hours. The reaction mixture was then cooled to ambient temperature. The product of the reaction was isolated in the form of a light colored liquid, with a yield of 191.0 grams and an acid number of 24.49 (mg KOH/g).

COMPARATIVE EXAMPLE 2

A 4,000 ml reaction flask having a 4-necked head was equipped with a heating mantle, an agitator shaft, a thermocouple, a nitrogen sparge tube, a Vigreux column, a condenser and a receiver. The reaction flask was charged with 991.0 grams of hexahydrophthalic anhydride, 1,596.2 grams of trimethylolpropane, 615.9 grams of phthalic anhydride, 51.0 grams of PolyFox™ PF-6320 di adipate synthesized via the method described in Comparative Example 1, and 1.6124 grams of butylstannoic acid. The reaction mixture was gradually heated with nitrogen sparge and agitation to a temperature of 210° C. over the course of 3.75 hours. The temperature was maintained in the range of 210-215° C. with agitation for an additional 15 hours, at which time the Vigreux column was removed and the reaction was continued until the expected amount of total condensate was collected, an additional 7.4 hours. The reaction mixture was cooled to 140° C. and the resulting polyester resin was diluted by gradually adding 1,441.1 grains of propylene glycol monomethyl ether acetate with agitation. The reaction yielded 4,354.4 grams of polyester polyol product in the form of a light colored, nearly opaque liquid. The polyester solution was analyzed and found to have a hydroxyl number of 192.0 (mg KOH/g), an acid number of 2.42 (mg KOH/g), 70.32% non-volatile material, a Gardner-Holdt viscosity of Z6+ at 332 seconds, a density of 9.45 pounds per gallon, and a Gardner color of less than 1. The calculated fluorine content of the undiluted polyester resin was 0.5%.

COMPARATIVE EXAMPLE 3

A non-fluorinated version of the polyester resin described in Comparative Example 2, commercially available from ETNA-TEC, Ltd. under the trade name TEC 2536, was included as a control in Examples 31-34. The polyester, supplied dissolved in a mixture of propylene glycol monomethyl ether acetate and xylene in a 6:1 ratio, was analyzed and found to have a hydroxyl number of 167.2 (mg KOH/g), an acid number of 1.87 (mg KOH/g), 64.90% non-volatile material, a Gardner-Holdt viscosity of Z5– at 127 seconds, a density of 9.28 pounds per gallon, and a Gardner color of less than 1.

EXAMPLE 31

Formulation and Physical Properties of Coatings Containing Fluorinated Polymers

The fluorinated polyester polyols of the invention, as well as representative polyester polyols from the comparative examples, were formulated into coatings for subsequent testing, as summarized in Table 1 (Formulation of Coating), below:

TABLE 1

|  | Ex. C3 | Ex. C2 | Ex. 21 | Ex. 9 | Ex. 10 | Ex. 24 | Ex. 28 |
| --- | --- | --- | --- | --- | --- | --- | --- |
| Raw Material (grams) | Resin | Resin | Resin | Resin | Resin | Resin | Resin |
| Resin | 40.40 | 40.40 | 40.40 | 40.40 | 40.40 | 40.40 | 40.40 |
| 1% Dibutyltin Dilaurate | 1.00 | 1.00 | 1.00 | 1.00 | 1.00 | 1.00 | 1.00 |
| PM Acetate | — | 19.00 | 19.00 | 19.00 | 19.00 | 19.00 | 19.00 |
| n-Butyl Acetate | 19.00 | — | — | — | — | — | — |
| Dimethyl Carbonate (DMC) | — | 15.00 | 15.00 | 15.00 | 15.00 | 15.00 | 15.00 |
| p-Chlorobenzotrifluoride | 15.00 | — | — | — | — | — | — |
| Tolonate ™ HDT-LV[1] | 23.12 | — | — | — | — | — | — |
| Tolonate ™ HDT-LV2[1] | — | 23.12 | 23.12 | 23.12 | 23.12 | 23.12 | 23.12 |
| Silquest ™ A-187[2] | — | 1.50 | 1.50 | 1.50 | 1.50 | 1.50 | 1.50 |
| 1% BYK ™-307[3] in DMC | — | 1.00 | 1.00 | 1.00 | 1.00 | 1.00 | 1.00 |
| Total Weight (grams) = | 98.52 | 101.02 | 101.02 | 101.02 | 101.02 | 101.02 | 101.02 |

[1]Polyisocyanate curative available from Vencorex Chemicals, Inc.
[2]Adhesion promoting additive available from Momentive Performance Materials, Inc.
[3]Wetting agent available from BYK-Chemie GmbH The coatings were sprayed onto test panels made from cold rolled steel (CRS) and dried for two hours at 180° F. The panels were subsequently tested for Pencil Hardness (ASTM D3363), Cross-Hatch Adhesion (ASTM D3359) and T-Bend (ASTM D4145). The results of the physical property testing are summarized in Table 2 (Physical Property Testing of Coatings), below:

TABLE 2

|  | Ex. C3 | Ex. C2 | Ex. 21 | Ex. 9 | Ex. 10 | Ex. 24 | Ex. 28 |
| --- | --- | --- | --- | --- | --- | --- | --- |
| Physical Property Test | Resin | Resin | Resin | Resin | Resin | Resin | Resin |
| Pencil Hardness (ASTM D3363) | H | H | H | H | H | 3H | 3H |
| Crosshatch Adhesion (ASTM D3359) | 4B | 5B | 5B | 5B | 5B | 5B | 5B |
| T-Bend Test (ASTM D4145) | Pass | Pass | Pass | Pass | Pass | Pass | Pass |

EXAMPLE 32

Anti-Stain Testing of Coatings Containing Fluorinated Polymers

The test panels prepared in Example 31 were each subjected to 14 staining agents for a period of 24 hours. Each panel was subsequently washed with a solution of soap in water and the residue of each stain was rated according to the following scale: 0=no residue; 1=faint residue; 2=moderate residue; and 3=strong residue. The results are summarized in Table 3 (Anti-Stain Testing of Coatings), below:

TABLE 3

|  | Ex. C3 | Ex. C2 | Ex. 21 | Ex. 9 | Ex. 10 | Ex. 24 | Ex. 28 |
| --- | --- | --- | --- | --- | --- | --- | --- |
| Staining Agent | Resin | Resin | Resin | Resin | Resin | Resin | Resin |
| Shoe Polish | 0 | 0 | 0 | 0 | 0 | 0 | 0 |
| Yellow Mustard | 0 | 0 | 0 | 0 | 0 | 0 | 0 |
| Brown Mustard | 0 | 0 | 0 | 0 | 0 | 0 | 0 |
| Ketchup | 0 | 0 | 0 | 0 | 0 | 0 | 0 |
| Coffee | 0 | 0 | 0 | 0 | 0 | 0 | 0 |
| Red Crayon | 0 | 0 | 0 | 0 | 0 | 0 | 0 |
| Orange Crayon | 0 | 0 | 0 | 0 | 0 | 0 | 0 |
| Brown Crayon | 0 | 0 | 0 | 0 | 0 | 0 | 0 |
| Green Crayon | 0 | 0 | 0 | 0 | 0 | 0 | 0 |
| Mauve Lipstick | 0 | 0 | 0 | 0 | 0 | 0 | 0 |
| Pink Lipstick | 0 | 0 | 0 | 0 | 0 | 0 | 0 |
| Sanford Sharpie™ - Black | 2 | 0 | 0 | 1 | 1 | 0 | 0 |
| BIC ™ Permanent Marker - Black | 2 | 0 | 0 | 0 | 0 | 0 | 0 |
| Grape Juice | 0 | 0 | 0 | 0 | 0 | 0 | 0 |

As is apparent from the results given above, the non-fluorinated resin from Example C3 results in relatively stain-resistant coatings. However, the fluorinated resins all show improved stain resistance in the case of the Sanford Sharpie™ and BIC™ Permanent Marker staining agents, with the fluorinated resins of the invention having the additional advantage of being transparent, in contrast to the fluorinated resin from Example C2.

As a more severe test of stain resistance, additional test panels were subjected to baked-on yellow mustard as the staining agent. Each panel was subjected to yellow mustard and baked at a given temperature for a given amount of time. The panels were then cleaned with a solution of soap in water and the residue of each stain was rated according to the following scale: 0=no residue; 1=trace of residue; 2=light residue; 3=moderate residue; and 4=strong residue. The results are summarized in Table 4 (Mustard Bake Anti-Stain Testing of Coatings), below:

TABLE 4

|  | Ex. C3 | Ex. C2 | Ex. 21 | Ex. 9 | Ex. 10 | Ex. 24 | Ex. 28 |
| --- | --- | --- | --- | --- | --- | --- | --- |
| Baking Conditions | Resin | Resin | Resin | Resin | Resin | Resin | Resin |
| 8 Minutes @ 150° F. | 2 | 1 | 0 | 0 | 0 | 1 | 1 |
| 10 Minutes @ 200° F. | 4 | 1 | 1 | 1 | 1 | 2 | 1 |
| 20 Minutes @ 200° F. | 4 | 2 | 2 | 2 | 2 | 2 | 2 |

The fluorinated resins all show improved stain resistance to baked on yellow mustard versus the non-fluorinated resin from Example C3, with the fluorinated resins of the invention having the additional advantage of being transparent, in contrast to the fluorinated resin from Example C2.

EXAMPLE 33

Dirt Pickup Resistance Testing of Coatings Containing Fluorinated Polymers

The coatings prepared in Example 31 were also subjected to an Accelerated Dirt Pickup Resistance Test procedure. Glass panels were treated with each of the coatings and dried for two hours at 180° F. A 55% red iron oxide slurry was made in water using R1599D Easy Dispersing Red Iron Oxide, available from Elementis Specialties, Inc. and subsequently brushed onto one half of each panel. The panels were then dried for one hour at room temperature, rinsed under lukewarm tap water and wiped with a paper towel. Samples were visually inspected to see if stains were present and then subjected to spectral analysis using a ColorTec PCM Color Meter to measure any residue (L; white-black; a: green-red; b: blue-yellow). The results of the spectral analysis, reported in the form of the percent change in each color parameter, are summarized in Table 5 (Accelerated Dirt Pickup Resistance Testing of Coatings), below:

TABLE 5

|  | Ex. C3 | Ex. C2 | Ex. 21 | Ex. 9 | Ex. 10 | Ex. 24 | Ex. 28 |
|---|---|---|---|---|---|---|---|
| Color Parameter | Resin | Resin | Resin | Resin | Resin | Resin | Resin |
| ΔL (%) | 0.49 | 1.65 | 0.49 | 1.10 | 0.92 | 0.18 | 0.72 |
| Δa (%) | 12.65 | 2.15 | 1.12 | 0.82 | 1.10 | 2.17 | 4.00 |
| Δb (%) | 14.17 | 2.92 | 7.72 | 16.73 | 3.21 | 2.97 | 5.15 |

The results, in general, show improved dirt pickup resistance for the fluorinated resins versus the non-fluorinated resin from Example C3, with the fluorinated resins of the invention having the additional advantage of being transparent, in contrast to the fluorinated resin from Example C2.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A method for making a functionalized fluorinated monomer by reacting at least one fluorinated alcohol and an alkyl or aryl halide, wherein the alkyl or aryl halide has at least two functional groups, wherein the functionalized fluorinated monomer is made by a reaction according to formula (XI):

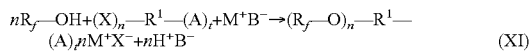

$nR_f$—OH+(X)$_n$—R$^1$—(A)$_t$+M$^+$B$^-$→(R$_f$—O)$_n$—R$^1$—(A)$_t$pM$^+$X$^-$+nH$^+$B$^-$ (XI)

wherein:
X is a halogen;
$R_f$ is a partially or fully fluorinated, branched or unbranched, substituted or unsubstituted alkyl group having one to about eighteen carbon atoms, and having 0 to 6 ether linkages, and when substituted includes a group selected from an aromatic group, a sulfur pentafluoride group, a halogen atom, and a combination thereof; or is a partially or fully fluorinated, substituted or unsubstituted aryl group, that when substituted includes a sulfur pentafluoride group, a halogen atom, or a combination thereof;
A is a functional group selected from hydroxyl, carboxylic acid, carboxylic acid ester, carboxylate salt, amine, and thiol;
$R^1$ is a saturated, branched or unbranched, substituted or unsubstituted alkyl group, cyclic alkyl group, or heterocyclic group having one to about twelve carbon atoms, and includes 0 to 6 ether linkages, ester linkages, or aryl groups; and
$M^+$ is a metal or other cation;
$B^-$ is a base;
t is 2 to 4; and
n is 1 to about 6.

2. The method of claim 1, wherein the reaction takes place via nucleophilic substitution.

3. The method of claim 2, wherein the alkyl or aryl halide molecule is a primary alkyl halide or a secondary alkyl halide.

4. The method of claim 1, wherein M$^+$B$^-$ is a base catalyst and the base catalyst comprises an alkoxide, a hydride or a hydroxide of an alkali or alkaline earth metal.

5. The method according to claim 1, wherein the functionalized fluorinated monomer has at least one hydroxyl group and the method further comprises reacting the functionalized fluorinated monomer having the at least one hydroxyl group with a cyclic reactant selected from the group of a cyclic carboxylic anhydride, a cyclic ether, a cyclic carbonate, and a cyclic ester to form a chain extended fluorinated monomer or a chain-extended fluorinated oligomer.

6. The method of claim 5, wherein the functionalized fluorinated monomer is a fluorinated diol having at least one ether linkage and the chain-extended fluorinated monomer is a fluorinated dicarboxylic acid.

7. The method according to claim 6, further comprising polymerizing the chain extended functionalized fluorinated monomer via condensation polymerization to form a fluorinated polyester.

8. The method of claim 5, wherein the cyclic reactant is a cyclic ether selected from the group of propylene oxide, glycidol, epichlorohydrin, butyl glycidyl ether, and 2-ethylhexyl glycidyl ether.

9. The method of claim 5, wherein the cyclic reactant is a cyclic ester selected from the group of L-lactide, D, L-lactide, glycolide, and ε-caprolactone.

10. The method of claim 9, wherein the cyclic reactant is ε-caprolactone.

11. The method of claim 5, wherein the cyclic reactant is a cyclic carbonate selected from the group of ethylene carbonate, propylene carbonate, and trimethylene carbonate.

12. The method of claim 11, wherein the cyclic reactant is trimethylene carbonate.

13. The method of claim 5, wherein the reactant is a cyclic carboxylic anhydride selected from the group of succinic anhydride, maleic anhydride, itaconic anhydride, aconitic anhydride, phthalic anhydride, hexahydrophthalic anhydride, trimellitic anhydride, and 1,2,4-cyclohexanetricarboxylic anhydride.

14. The method of claim 5, further comprising reacting the chain extended fluorinated monomer or oligomer with a cyclic ester, cyclic carbonate, or a cyclic ether via ring opening polymerization to form a fluorine-containing polyester polyol, a fluorine-containing polycarbonate polyol or a fluorine-containing polyether polyol.

15. The method according to claim 1, wherein the functionalized fluorinated monomer has at least one hydroxyl group and the method further comprises reacting the functionalized fluorinated monomer having the at least one hydroxyl group with a cyclic ester, cyclic carbonate, or a cyclic ether via ring opening polymerization to form a fluorine-containing polyester polyol, a fluorine-containing polycarbonate polyol or a fluorine-containing polyether polyol, respectively.

16. The method according to claim 1, further comprising:

reacting the at least one functional group of the functionalized fluorinated monomer with either or both of: a reactive end group on a polymer or oligomer or a reactive functional group on a backbone of the polymer or oligomer to modify the polymer or oligomer.

17. The method of claim 16, wherein the functional group of the functionalized fluorinated monomer is a hydroxyl group and the reactive functional group of the polymer or oligomer is a cyclic anhydride, and wherein the polymer or oligomer is selected from free radically polymerized copolymers of maleic anhydride with one or more of styrene, methyl methacrylate, butadiene and ethylene.

18. The method of claim 16, wherein the functional group A of Formula XI of the functionalized fluorinated monomer is a carboxylic acid group and the reactive functional group of the polymer or the oligomer is an epoxide group, and wherein the polymer or oligomer is selected from copolymers of glycidyl acrylate and/or glycidyl methacrylate, epoxy resins, polymers and copolymers of bisphenol A diglycidyl ether.

19. The method of claim 16, wherein the functional group A of Formula XI of the functionalized fluorinated monomer is an amino group and the reactive functional group of the polymer or oligomer is a cyclic anhydride group derived from maleic anhydride, an isocyanate or an epoxide, and wherein the polymer or oligomer is a free radically polymerized copolymer of maleic anhydride with one or more of styrene, methyl methacrylate, butadiene, and ethylene, a polyisocyanate, a copolymer of glycidyl acrylate or glycidyl methacrylate or a polymer or oligomer of bisphenol A diglycidyl ether.

20. The method of claim 1, Wherein $R_f$ has a structure according to the following formula:

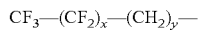

wherein x is from 0 to about 10, and y is from 1 to about 10, More preferably, x is from 0 to about 5, and y is preferably from 0 to about 10.

21. The method of claim 20, wherein:
x=0, 1, 3 or 5; and
y=1 or 2.

22. The method of claim 1, wherein $R_f$ is chosen from the following structures:

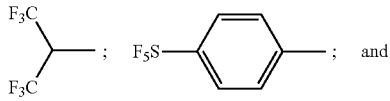

-continued

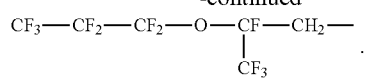

23. The method of claim 1, wherein $R^1$ is chosen from the following structures:

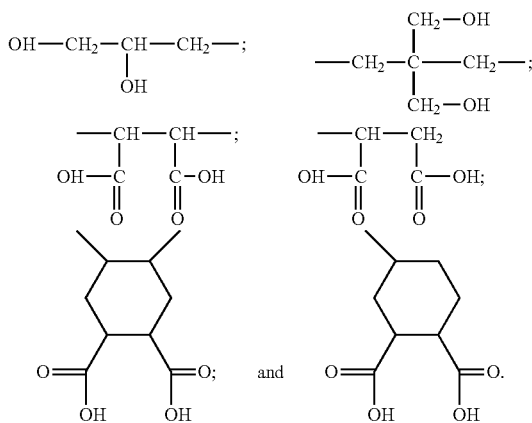

24. The method of claim 1, wherein the base catalyst ($M^+B^-$) comprises an alkoxide, a hydride or a hydroxide of an alkali or alkaline earth metal.

* * * * *